United States Patent
Ninomiya et al.

(10) Patent No.: US 8,188,740 B2
(45) Date of Patent: May 29, 2012

(54) MAGNETIC RESONANCE IMAGING APPARATUS

(75) Inventors: Atsushi Ninomiya, Ome (JP); Yoshimi Kasai, Nagareyama (JP); Hisaaki Ochi, Kodaira (JP); Masayoshi Dohata, Yokohama (JP); Yoshiyuki Miyamoto, Abiko (JP); Shizuka Nagai, Kashiwa (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 37 days.

(21) Appl. No.: 12/521,336

(22) PCT Filed: Dec. 26, 2007

(86) PCT No.: PCT/JP2007/074937
§ 371 (c)(1),
(2), (4) Date: Oct. 26, 2010

(87) PCT Pub. No.: WO2008/081808
PCT Pub. Date: Jul. 10, 2008

(65) Prior Publication Data
US 2011/0031970 A1  Feb. 10, 2011

(30) Foreign Application Priority Data
Dec. 28, 2006  (JP) .................. 2006-353697

(51) Int. Cl.
G01V 3/00  (2006.01)
(52) U.S. Cl. ........................ 324/318; 324/322
(58) Field of Classification Search .......... 324/300–322; 600/407–445
See application file for complete search history.

(56) References Cited

U.S. PATENT DOCUMENTS
4,727,327 A * 2/1988 Toyoshima et al. ........... 324/309
(Continued)

FOREIGN PATENT DOCUMENTS
JP  2002-153440  5/2002
JP  2003-079595  3/2003
WO  WO 03/024327 A1  3/2003

OTHER PUBLICATIONS

J. B. Ra, C.Y. Rim: "Fast Imaging Using Subencoding Data Sets from Multiple Detectors", Magnetic Resonance in Medicine, vol. 30, pp. 142-145 (Mar. 1993).

(Continued)

Primary Examiner — Brij Shrivastav
(74) Attorney, Agent, or Firm — Antonelli, Terry, Stout & Kraus, LLP.

(57) ABSTRACT

The present invention provides a vertical magnetic field MRI apparatus which is capable of speeding up imaging for taking an image of any cross section of a wide area such as a total body, while suppressing increase of the number of channels and maintaining high sensitivity in a deep portion of a subject. A receiver coil unit 500 incorporates a bed coil unit 600 whose longitudinal direction agrees with a body axis direction of the test object 103, and an upper coil unit 700 which is detachably mounted on the bed coil unit 600. The bed coil unit 600 is provided with a carrying surface 601 for placing the test object 103 thereon and multiple lower sub-coils arranged in a lower part of the carrying surface 601, and the upper coil unit 700 is provided with multiple upper sub-coils which are connected to the lower sub-coils. The upper sub-coils are separated into two parts; one arranged in a flexible inner support 20-1 covering the installation surface 601 and another arranged in a flexible outer support 20-2 covering the external side of the inner support 20-1. The upper sub-coils and the lower sub-coils are connected by mounting the upper coil unit 700 on the bed coil unit 600, thereby forming the multiple types of sub-coils.

13 Claims, 30 Drawing Sheets

U.S. PATENT DOCUMENTS

| | | | |
|---|---|---|---|
| 7,012,426 B2 * | 3/2006 | Edwards et al. | 324/303 |
| 7,808,241 B2 * | 10/2010 | Dohata et al. | 324/318 |
| 2004/0061498 A1 | 4/2004 | Ochi et al. | |
| 2005/0030022 A1 | 2/2005 | Robb et al. | |
| 2007/0244388 A1 * | 10/2007 | Sato et al. | 600/424 |
| 2010/0244829 A1 * | 9/2010 | Zenge | 324/309 |
| 2011/0015078 A1 * | 1/2011 | Gao et al. | 505/162 |

OTHER PUBLICATIONS

Klaas P. Pruessmann, Markus Weiger, Markus B. Scheidegger, and Peter Boesiger: "SENSE: Sensitivity Encoding for Fast MRI", Magnetic Resonance in Medicine, vol. 42, pp. 952-962 (Jul. 1999).

* cited by examiner

FIG. 7
(A)
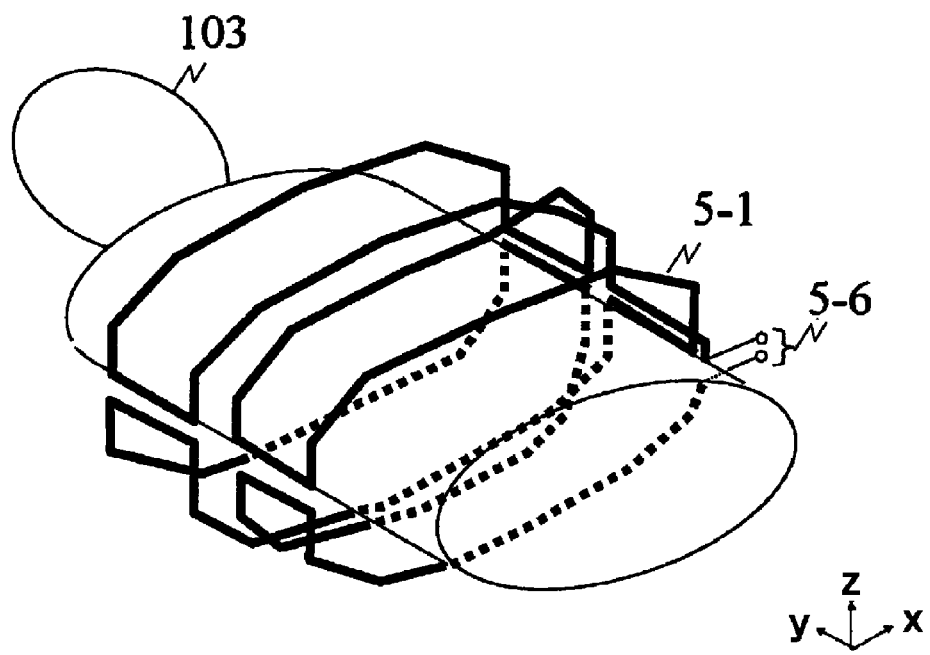
(B)
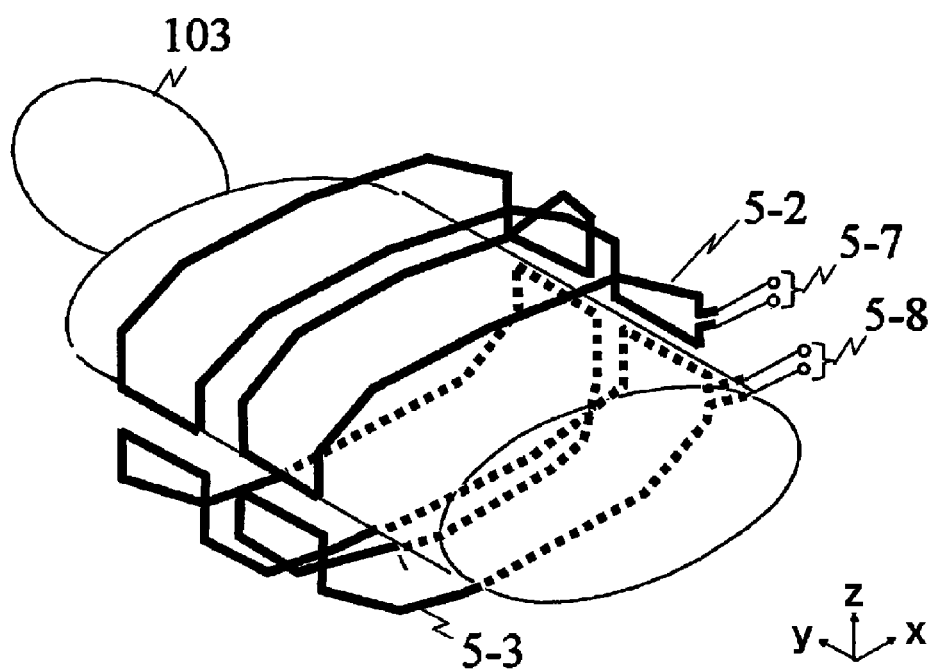

FIG.10
(A)
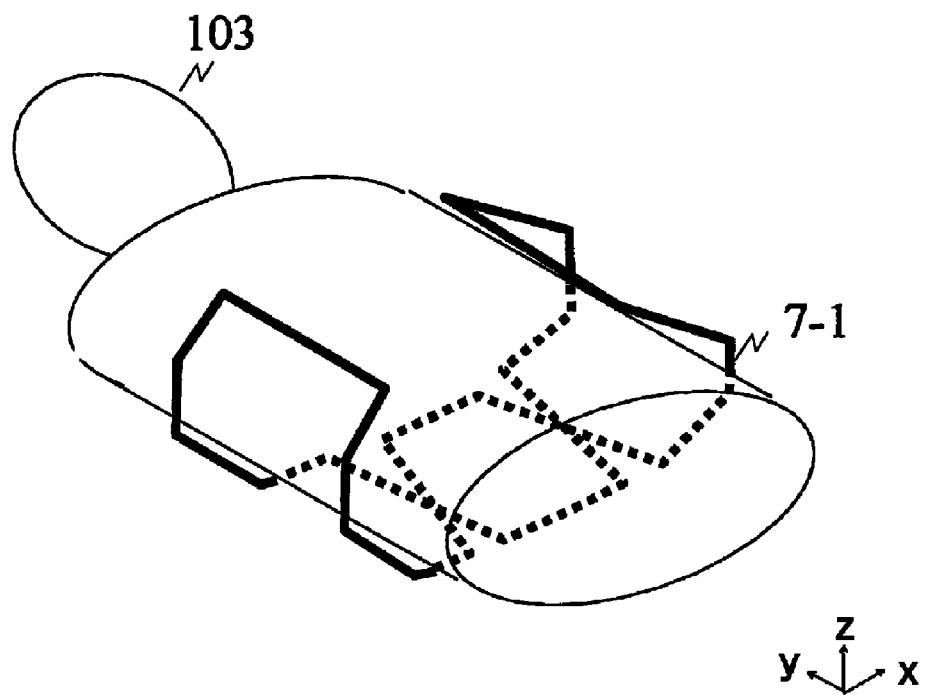
(B)
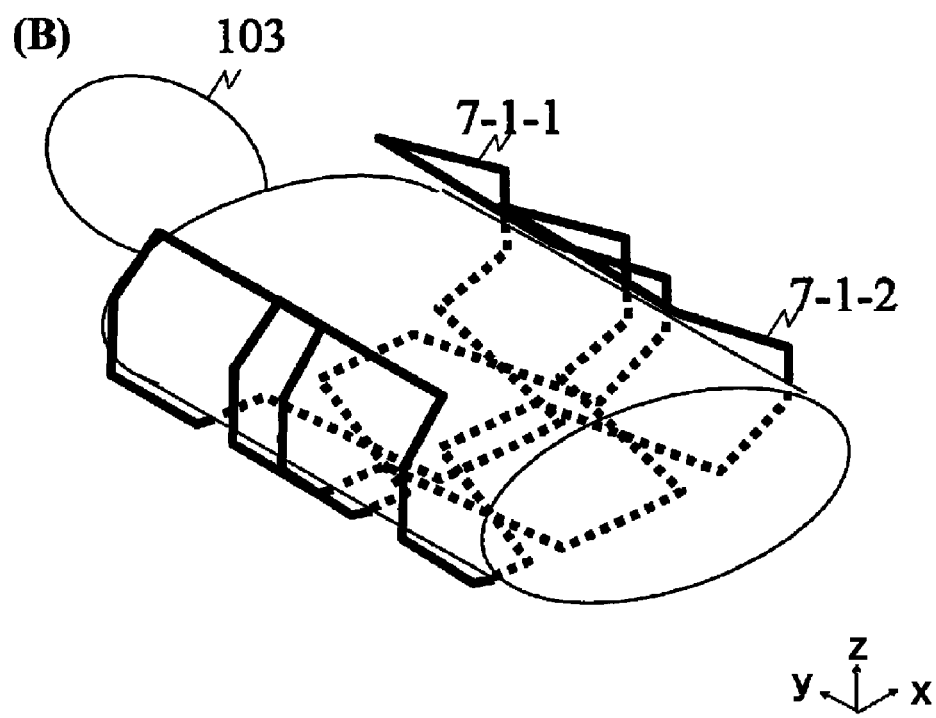

FIG. 12
(A)
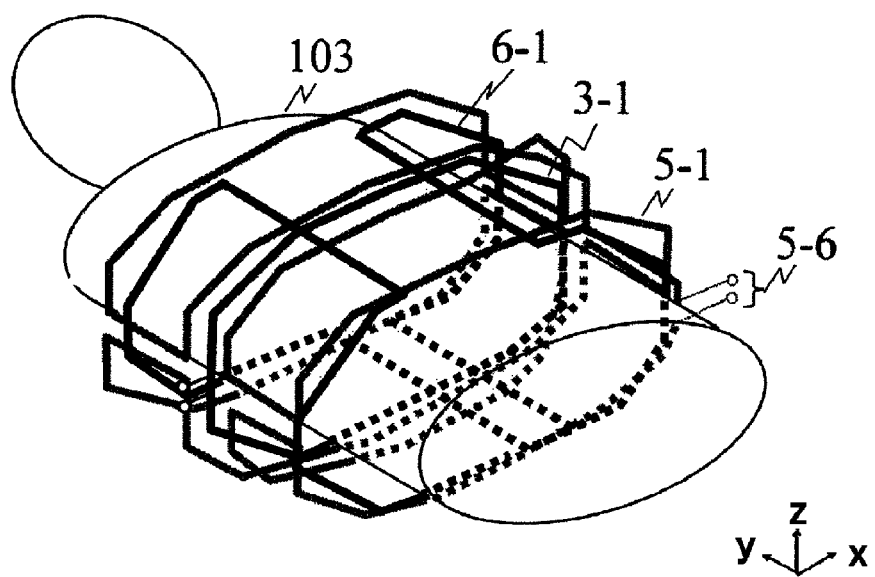
(B)
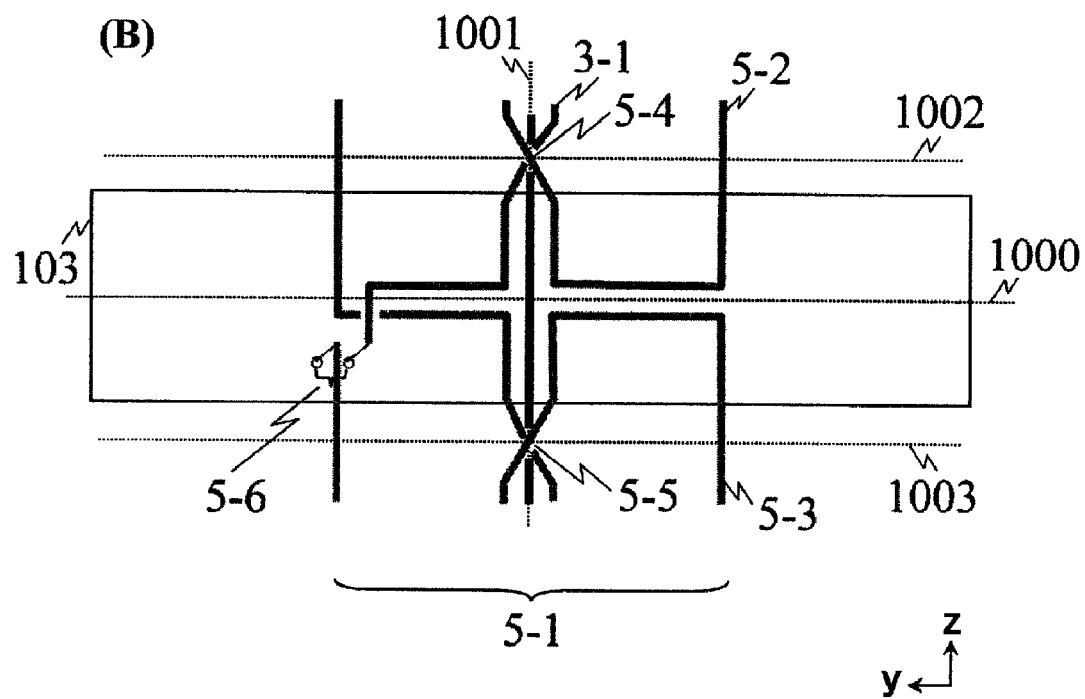

FIG. 13
(A)
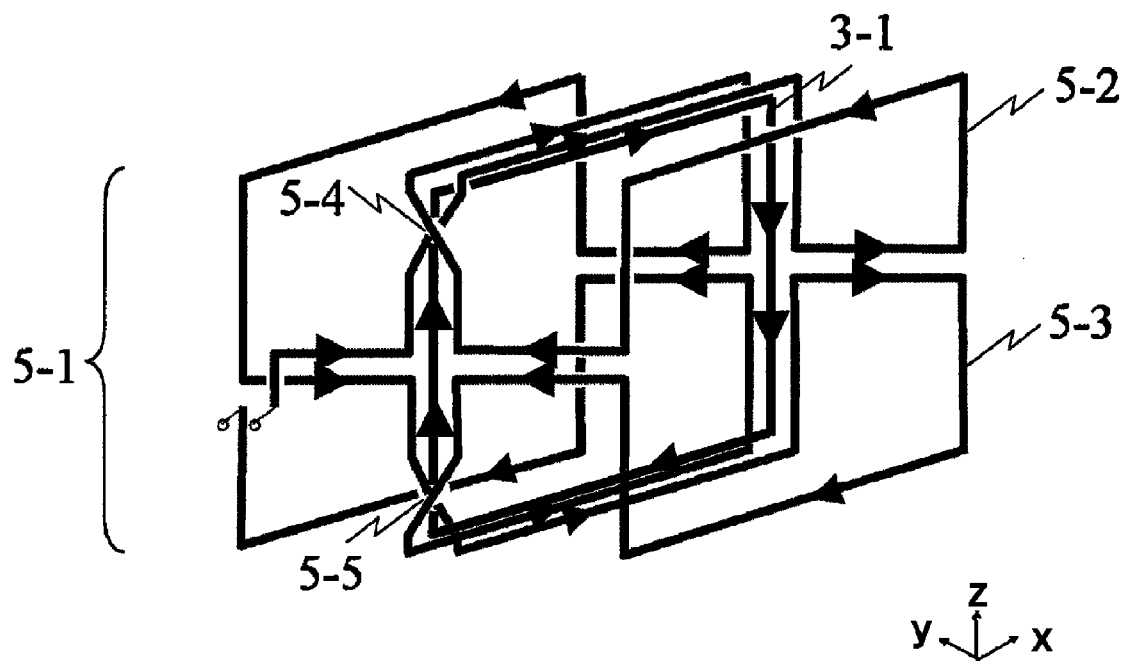
(B)
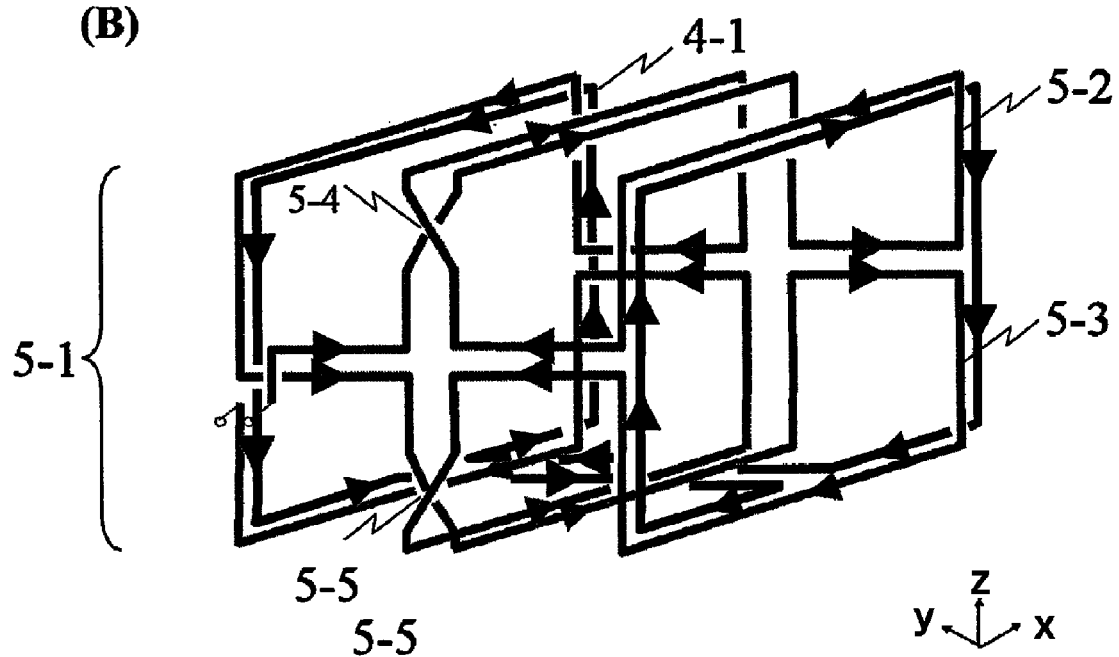

FIG.17
(A)
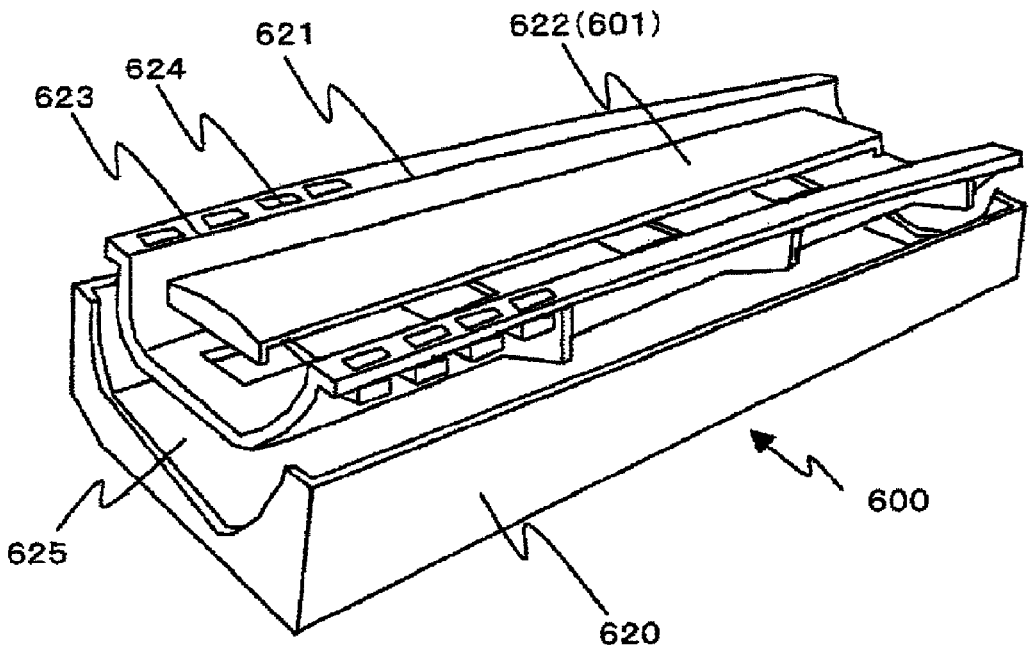
(B)
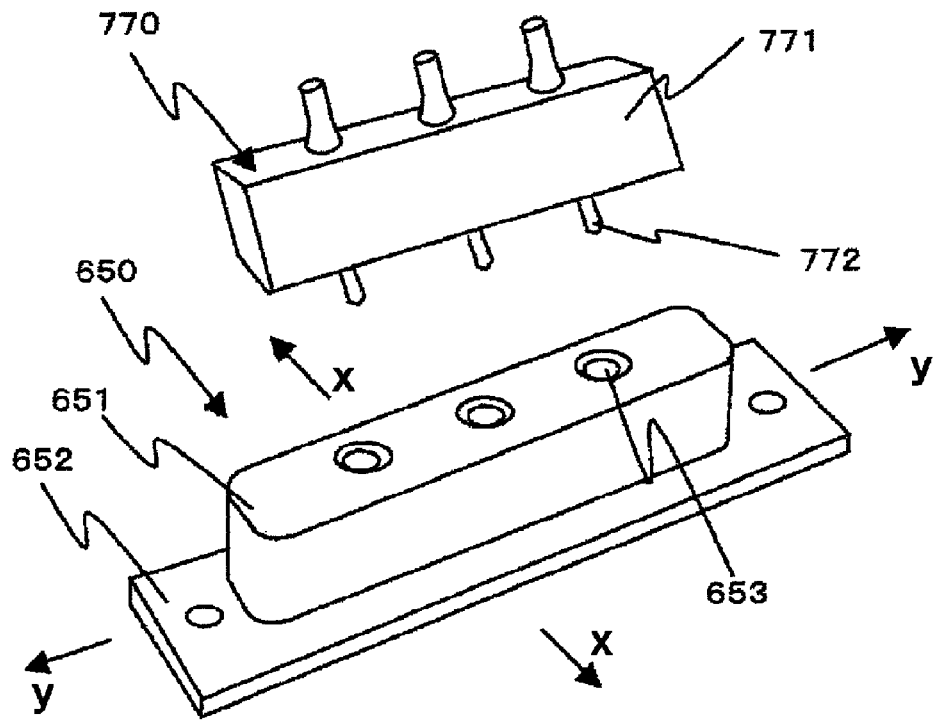

FIG.21
(A)
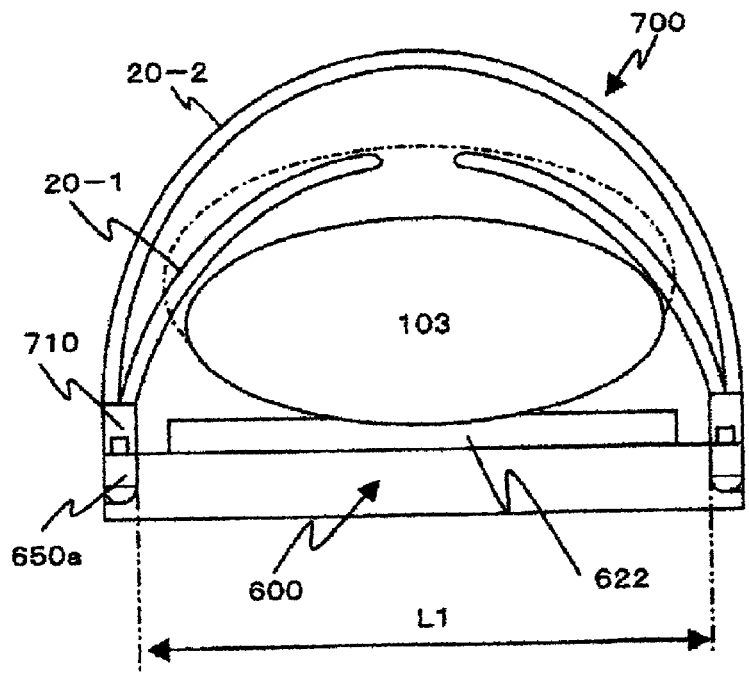
(B)
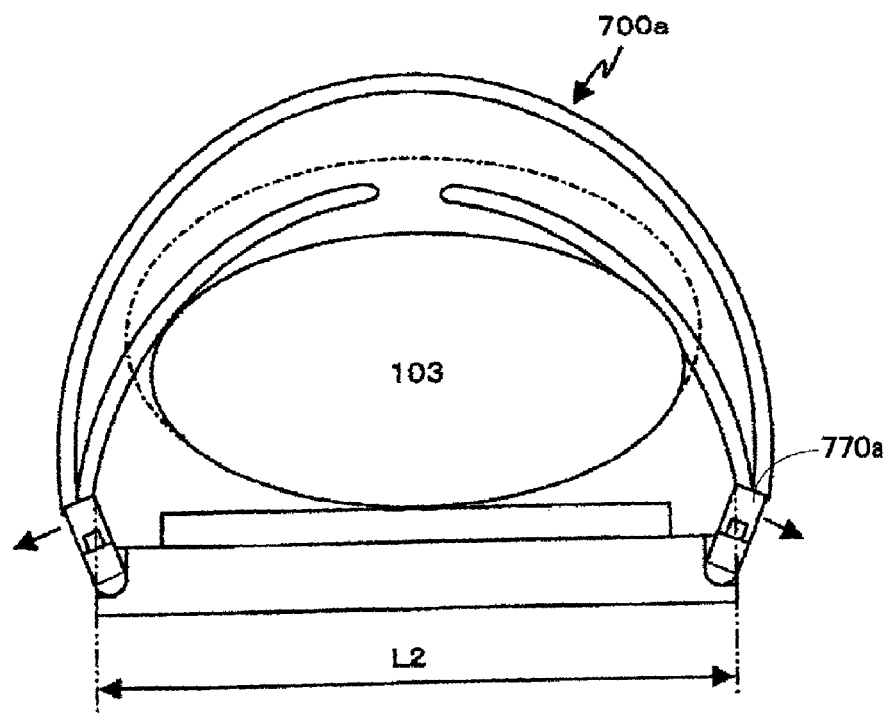

FIG.27
(A)
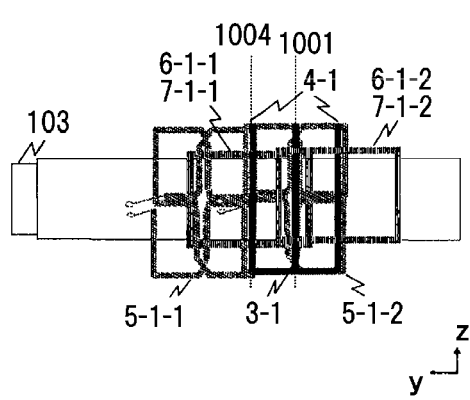
(B)
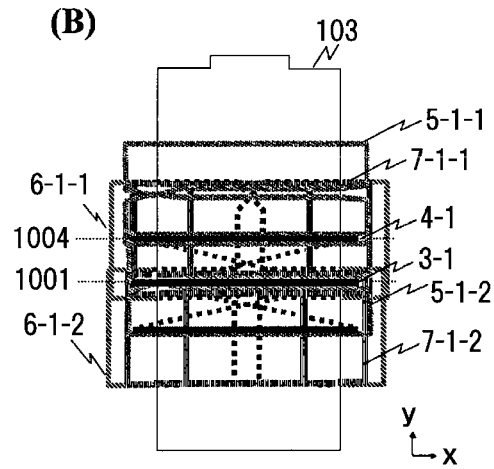
(C)
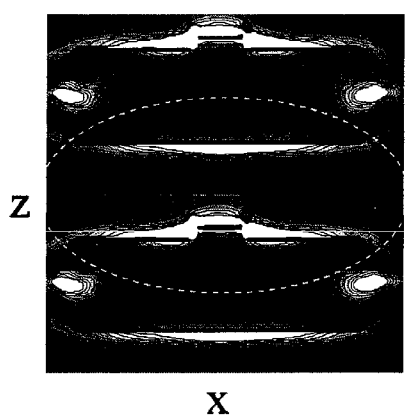
(D)
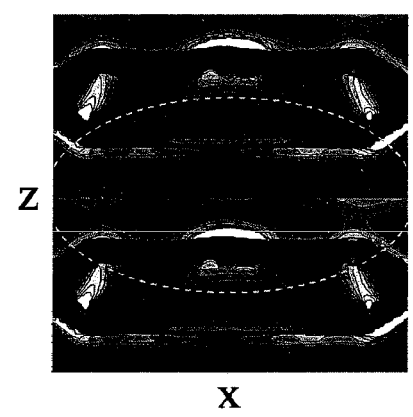
(E)
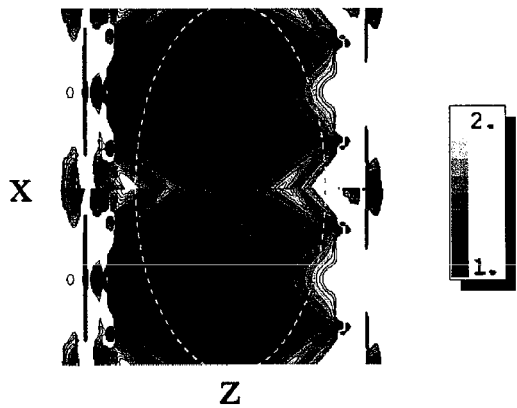
(F)
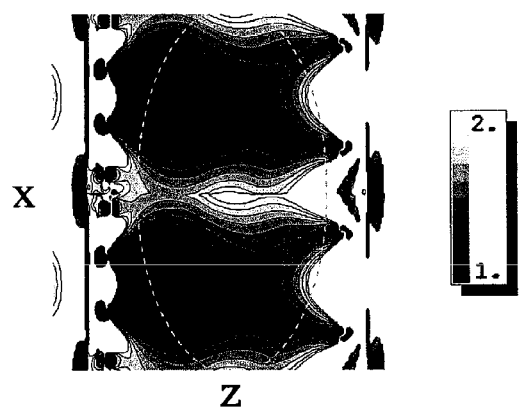

FIG. 28
(A)
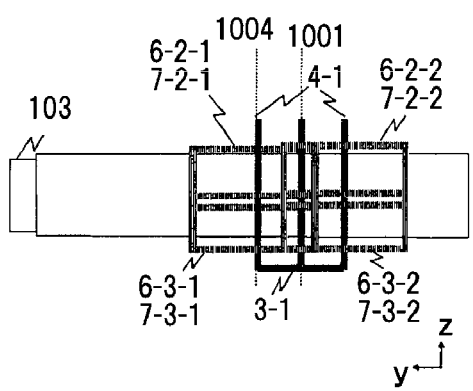
(B)
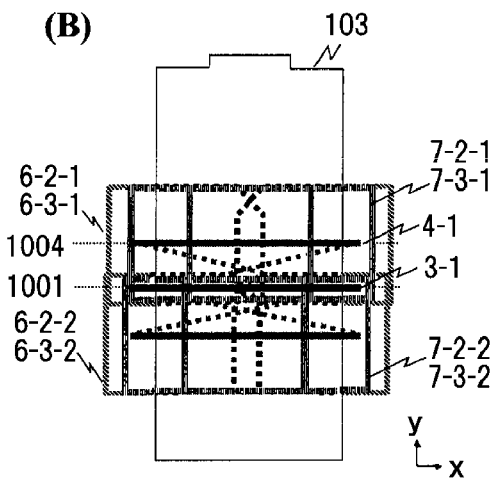
(C)
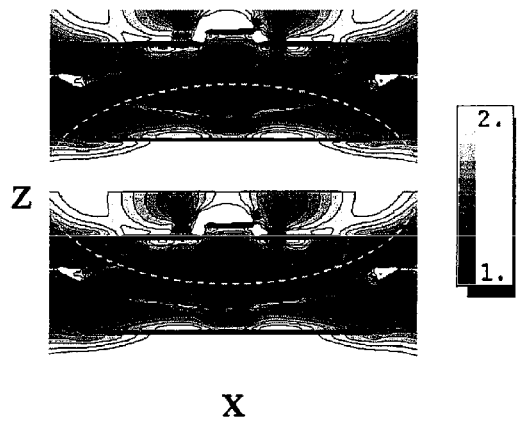
(D)
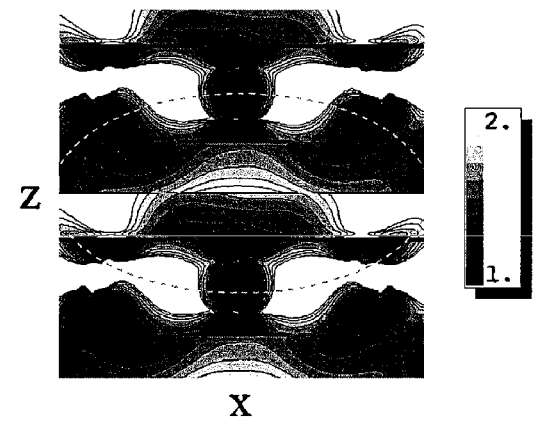
(E)
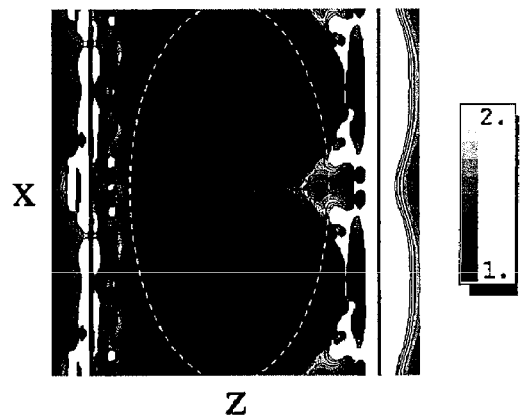
(F)
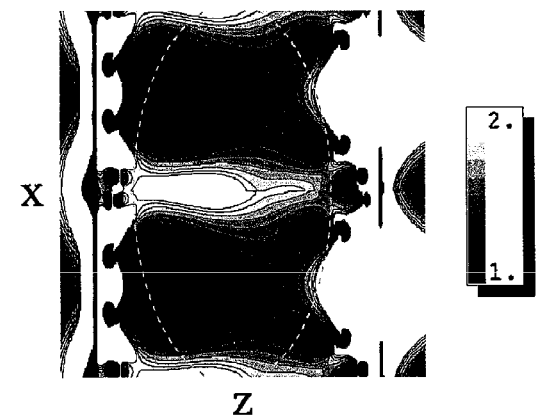

FIG.29
(A)
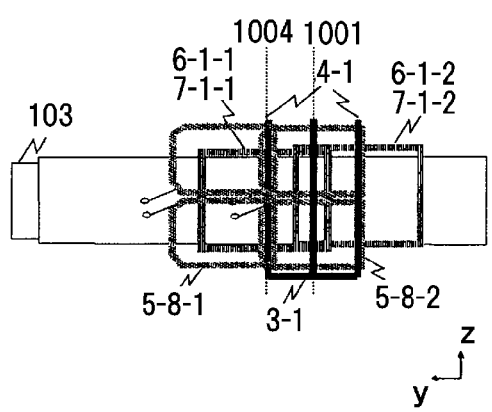
(B)
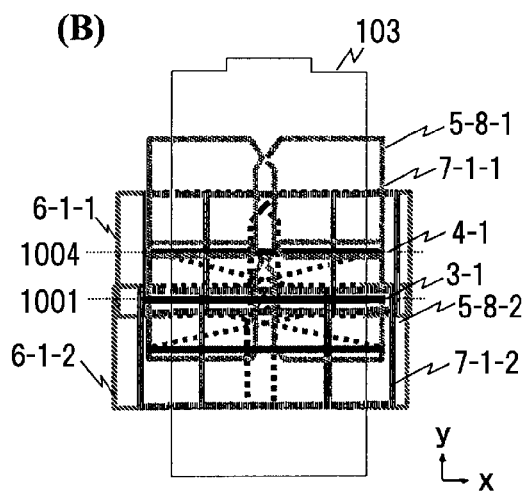
(C)
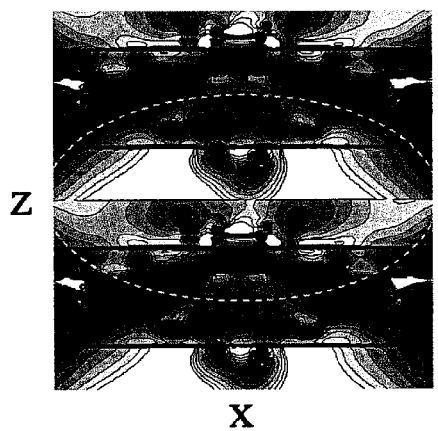 
(D)
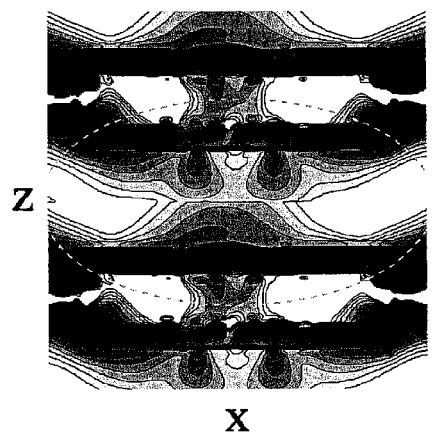 

MAGNETIC RESONANCE IMAGING APPARATUS

TECHNICAL FIELD

The present invention relates to a magnetic resonance imaging apparatus (MRI apparatus), and in particular, it relates to an vertical magnetic field type MRI apparatus, and an RF receiver coil for detecting a nuclear magnetic resonance signal which is suitable for the vertical magnetic field type MRI apparatus.

BACKGROUND ART

In the MRI apparatus, a test object is placed in homogeneous static magnetic field space, and imaging of the test object is performed by using nuclear magnetic resonance. An imaging region is limited to the static magnetic field space. In recent years, a method for imaging a total body has been developed, which moves a table (bed) on which the test object is placed, and now attention is particularly given to attempts of a total body screening by use of the MRI.

When measurement is performed as to a wide area such as the total body, it is desired to implement a receiver coil which is able to keep high sensitivity across the wide area, and simultaneously, it is also desired to shorten a time length necessary for the imaging, so as to make the measurement time to be within a range tolerable for the subject. As a technique for shortening the imaging time of the diagnostic MRI, a technique for developing image aliasing using sensitivity distributions from multiple RF coils (this technique being called as "parallel imaging", and hereinafter, it will be referred to as "parallel imaging") is coming into practical use (non patent document 1). In this method, a receiver coil made up of multiple sub-coils is used to perform simultaneous signal measurement, and the imaging time is shortened to a time length obtained by dividing original imaging time by the number of sub-coils.

In order to achieve the parallel imaging, it is necessary that electromagnetic coupling between the multiple sub-coils is sufficiently small. If there exists electromagnetic coupling between the sub-coils, noise interference may occur between the coils, and this may deteriorate an image S/N. Next, it is also necessary that the multiple sub-coils have to be arranged properly. If the arrangement of the sub-coils is not proper, the image S/N may be deteriorated partially. As one of the evaluation criteria to decide whether or not the arrangement of the sub-coils is appropriate, there is a standard referred to as Geometry factor (hereinafter, it will be abbreviated as "G factor") (a calculation formula is described in non patent document 2). The G factor is a numerical value equal to or larger than 1.0 derived from a sensitivity distribution on an imaging plane as to each of the sub-coils, and the S/N at each position of an image is proportional to (1/(G factor)). Therefore, it is preferable that the G factor of the image at a part where the subject exists is as small as possible. At least, the value is desired to be smaller than 2.0, typically. As thus described, in order to design a receiver coil used for the parallel imaging, it is necessary to reduce the electromagnetic coupling between the multiple sub-coils used for the simultaneous measurement, and it is also necessary to find out a coil arrangement which allows the G factor to be a small value on all over the imaging plane. The parallel imaging has been developed mainly for a horizontal magnetic field apparatus having a high magnetic field, and various receiver coils are prepared for the horizontal magnetic field apparatus.

On the other hand, as for a vertical magnetic field open MRI apparatus, with its enhanced openness of magnet, the subject is directly accessible, and it is suitable for a usage as an interventional MRI. The direction of an RF magnetic field generated by the RF coil has to be orthogonal to the direction of the static magnetic field. Therefore, when the direction of the static magnetic field is changed from horizontal to vertical, it is necessary to change the receiver coil configuration as well. In the vertical magnetic field type MRI apparatus, because the direction of the static magnetic field is vertical, a subject is typically laid down in the horizontal direction when tested, and therefore a solenoid coil which is arranged around the outer periphery of the subject can be used. The solenoid coil which is arranged around the subject provides a strong sensitivity even in a deep portion of the subject, unlike a loop coil placed on the surface of the subject. Therefore, if the magnetic field strength is the same, the vertical magnetic field type MRI, in which the solenoid coil is usable, typically provides higher sensitivity in a deep portion of the subject, rather than the horizontal magnetic field type MRI.

By way of example, the patent document 1 and patent document 2 suggest the arrangement of the receiver coil which is compliant with the vertical magnetic field. The patent document 1 discloses a method for imaging with a high sensitivity and at a high speed with an application of parallel imaging, as to an area in proximity to a heart which is a deep portion of the subject, by using a combination of multiple solenoid coils arranged around the outer periphery of the subject and surface coils. The patent document 2 discloses that by using a solenoid and a saddle coil being orthogonal to each other, sensitivity in a deep portion of the subject is enhanced, and at least two sub-coils are arranged in opposed manner in each of the three directions of the subject, thereby forming a sensitivity profile of the sub-coils in the phase encoding direction of each of the three directions. By using the receiver coils with the arrangement as described above, it is possible to obtain high sensitivity even in a deep portion of the subject, and any phase encoding direction can be selected to achieve a high-speed imaging.

Non patent document 1
J. B. Ra, C. Y. Rim: "Fast Imaging Using Subencoding Data Sets from Multiple Detectors", Magnetic Resonance in Medicine, vol. 30, pp. 142-145 (1993)

Non patent document 2
Klaas P. Pruessmann, Markus Weiger, Markus B. Scheidegger, and Peter Boesiger: "SENSE: Sensitivity Encoding for Fast MRI", Magnetic Resonance in Medicine, vol. 42, pp. 952-962 (1999).

Patent document 1
Japanese Unexamined Patent Application Publication No. 2002-153440

Patent document 2
Japanese Unexamined Patent Application Publication No.

DISCLOSURE OF THE INVENTION

Problem to be Solved by the Invention

However, the coil arrangement as described in the patent document 1 and the patent document 2 has a restriction in arranging the sub-coils when a total body is imaged. By way of example, if multiple coils are arranged in the body axis direction of the subject, additional modification is necessary for the coil arrangement described in the patent document 1, due to a structural restriction. When the coils are implemented across the total body according to the arrangement described in the patent document 2, a large number of auxiliary coils may be necessary in order to reduce the electromagnetic coupling between the opposed sub-coils. In other words, modifications of the above coil arrangement to achieve a total-body use arrangement may bring about the possibility of increase in the number of channels.

Therefore, an object of the invention is to achieve a receiver coil usable in a vertical magnetic field type MRI apparatus, which provides high sensitivity in a deep portion of a subject, and which is capable of performing a high-speed imaging of any cross section in a wide area such as a total body, with sub-coils having a relatively small number of channels. Another object is to provide a receiver coil with a good mountability.

Means to Solve the Problem

The magnetic resonance imaging apparatus to solve the problems above includes a static magnetic field generation means for generating a static magnetic field in a vertical direction, an imaging means for applying an RF magnetic field and a gradient magnetic field to a test object placed in the static magnetic field, and a receiving means for receiving a nuclear magnetic resonance signal generated from the test object, the receiving means being provided with a receiver coil unit made up of multiple types of sub-coils, wherein, the receiver coil unit comprises a bed coil unit whose longitudinal direction agrees with a body axis direction of the test object, and an upper coil unit which is detachably mounted on the bed coil unit, the bed coil unit is provided with a carrying surface for placing the test object thereon and multiple lower sub-coils arranged in a lower part of the carrying surface, the upper coil unit is provided with multiple upper sub-coils which are connected to the lower sub-coils, and the upper sub-coils and the lower sub-coils are connected by mounting the upper coil unit on the bed coil unit, thereby forming the multiple types of sub-coils.

BEST MODE FOR CARRYING OUT THE INVENTION

Hereinafter, with reference to FIG. 1 to FIG. 30, a detailed explanation will be made regarding a magnetic resonance imaging apparatus (referred to as MRI apparatus) and a receiver coil which is mounted on the MRI apparatus, according to the present embodiment. Figures from FIG. 1 to FIG. 29 illustrate a first embodiment, and FIG. 30 illustrates a second embodiment. In the first embodiment, FIG. 1 schematically illustrates the MRI apparatus, FIG. 2 shows a block diagram of the MRI apparatus, FIG. 3 to FIG. 15 illustrate a principle of operation of the receiver coil, FIG. 16 to FIG. 23 illustrate external structure of the receiver coil unit, FIG. 24 to FIG. 26 are explanatory views of a control of the receiver coil, and FIG. 27 to FIG. 29 are explanatory views of simulation of the receiver coil.

First Embodiment

Initially, with reference to FIG. 1, a schematic structure of the MRI apparatus according to the present embodiment will be explained. FIG. 1 illustrates a schematic structure of the MRI apparatus.

In FIG. 1, the MRI apparatus according to the present embodiment comprises an MRI apparatus main unit 50 provided with a pair of magnets 101 placed above and below for generating a static magnetic field in the vertical direction z indicated by arrow z, a bed part 60 for inserting a subject (test object 103) into the static magnetic field in the vertical direction z of the MRI apparatus main unit 50, and other elements not illustrated, such as a power supply unit, a computer for processing images and the like.

The MRI apparatus main unit 50 is provided with an upper main body 51 and a lower main body 52 incorporating the magnets 101, and a support part 53 on the upper part of the lower main body 52, for connecting and supporting the upper main body 51. There is formed space having a predetermined size for inserting the test object 103 between the upper main body 51 and the lower main body 52. On the top surface of the lower main body 52, there is formed a flat table surface 54 onto which the test object 103 is inserted.

The bed part 60 comprises a top board 61 for placing the test object 103 thereon, a bed housing 62 for supporting the top board 61 above the floor surface, and the top board 61. The bed housing 62 is provided with an elevating function not illustrated, and when the test object 103 is installed, it is lowered, and when an inspection is performed for the test object 103 placed thereon, it is movable to a position where a sliding surface formed on the bottom of the top board 61 is made slidable onto the table surface 54. Furthermore, this bed housing 62 is provided with a sliding mechanical part, not illustrated, which inserts the top board 61 into the static magnetic field of the vertical direction along the longitudinal direction (y1).

The bed moving direction y1 is the same as the longitudinal direction of the top board 61, and also the same as the body axis direction y of the test object 103 placed on the top board 61. That is, with respect the static magnetic field direction (vertical direction) z-direction, the left-right direction x of the test object 103 and the body axis direction y of the test object 103 are orthogonal to each other.

One significant feature of the present embodiment is that a receiver coil unit 500 is mountable on the top board 61 or mountable substituting for the top board 61, the receiver coil providing high sensitivity in a deep portion of the subject and being capable of high-speed imaging to take an image of any cross section of a large area such as a total body.

This receiver coil unit 500 comprises a bed coil unit 600, and multiple upper coil units 700 mounted on the bed coil unit 600 in a detachable manner. The bed coil unit 600 has a thin plate-like appearance with an upper surface of rectangular shape, whose longitudinal direction agrees with the y-direction. In the center the bed coil unit, there is provided an installation surface 601 for placing the test object 103, and on the both sides thereof, multiple joint support parts 650 are provided, which are formed along the y-direction. On the lower part of the installation surface 601, multiple coils not illustrated, are communicated with the joint support parts 650 and arranged in the x-direction.

On the other hand, the upper coil unit 700 includes a pair of joining sections 710 arranged on the both sides, an outer support 20-2, both ends of which are mounted respectively on the pair of the joining sections 710, and a pair of inner supports 20-1, one end of which is mounted on the joining section 710, and the other end of which is a free end. The joining section 710 has a stick-like appearance, and along the longitudinal direction thereof, multiple joint parts 770 are provided, which are supposed to be connected with the joint support parts 650. The inner support 20-1 and the outer support 20-2 have appearances of thin plate, inside which coils are arranged, and in each of the supports, multiple openings 550 are formed in accordance with the arrangement of coils.

The upper coil unit 700 is capable of being connected with the bed coil unit 600 via a linkage between the joint support parts 650 and the joint parts 770. With this linkage, a group of multiple coils is formed to cover an external side of the test object 103 placed on the installation surface 601.

In the present embodiment, the group of coils arranged on the bed coil unit 600 is divided into multiple blocks each having the same coil arrangement, along the y-direction. In the example as shown in FIG. 1, they are divided into three blocks along the y-direction. Then, in the present embodiment, one upper coil unit 700 can be mounted on one of the blocks, and with the linkage of this single block, a portion of the test object 103, which is covered by the single block, can be subjected to inspection.

In the present embodiment, three upper coil units 700 are prepared, and these are mounted on the bed coil unit 600 to arrange a group of coils in the body axis direction y of the test object 103, and therefore, the total body of the test object 103 can be inspected. For example, these blocks are turned ON and OFF sequentially as appropriate, along with insertion of the body into the static magnetic field in the vertical direction z, thereby enabling the total body inspection of the test object 103.

One of the other significant features of the present embodiment is that the groups of the multiple coils covering the outer periphery of the test object 103 are divided into two, one being arranged in the inner support 20-1 and another being arranged in the outer support 20-2. In the receiver coil unit 500 according to the present embodiment, five types of sub-coils, each being more than one, are arranged along the y-direction (body axis direction of the subject), in order to provide high sensitivity in the deep portion of the subject and to perform high-speed imaging to take an image of any cross section of a wide area such as the total body.

In the present embodiment, the five types of sub-coils include, a first type sub-coil 3-1 (see FIG. 5) made up of a solenoid coil arranged around the outer periphery of the test object 103, a second type sub-coil 4-1 (see FIG. 6) made up of sub-coil 4-1 forming two current loops around the outer periphery of the test object 103, a third type sub-coil 5-1 (see FIG. 7) made up of two coils having almost the same shape arranged in the front and rear of (in the z-direction of) the test object 103 in a manner opposed to each other, a fourth type sub-coil 6-1 (see FIG. 9) made up of a coil (saddle coil) having two current loops arranged on the surface of the test object 103, and a fifth type sub-coil 7-1 (see FIG. 10) made up a coil having three current loops arranged on the surface of the test object 103.

This group of sub-coils can be divided into two: one consists of the first type sub-coil 3-1, the second type sub-coil 4-1, and the third type sub-coil 5-1, as to which a coil pattern (conductor) exists above the test object 103; and another consists of the fourth type sub-coil 6-1 and the fifth type sub-coil 7-1, as to which the coil pattern (conductor) does not exist above the test object 103. In the present embodiment, the three coils having the coil patterns (conductors) above the test object 103 are arranged within the outer support 20-2, and the two coils not having the coil patterns (conductors) above the test object 103 are arranged within the inner support 20-1. It is a matter of course that the bed coil unit 600 is provided with a coil arrangement which brings the five types of sub-coils to completion, by mounting the inner support 20-1 and the outer support 20-2 thereon.

Since the present embodiment employs the structure as described above, the inner support 20-1 can be opened above the test object 103, and on the other hand, the external side of the inner support can be covered by the arc-like outer support 20-2.

One of the other significant features of the present embodiment is that the inner support 20-1 and the outer support 20-2 are made of a material having flexibility. In the present embodiment, the joining section 710 is made of an ABS resin material with hardness, and the inner support 20-1 and the outer support 20-2 are formed by surrounding the coils by a urethane material. Therefore, the inner support 20-1 which is separated to both sides above the test object 103 uses the softness to cover the upper part of the test object 103 in such a manner as tightly adhering thereto. On the other hand, the outer support 20-2 is mounted in such a manner that the both ends thereof are held by the bed coil unit 600. Therefore, it is possible to protect the external side of the inner support 20-1 with certain strength in a form of arc.

Then, in the present embodiment, since the inner support 20-1 and the outer support 20-2 are made of a material having flexibility, after the upper coil unit 700 is detached from the bed coil unit 600, it is possible to fold the coil to be flat. Accordingly, the receiver coil, which has conventionally a fixed shape having difficulty in storage, is now changed to be a shape allowing for easy storage.

Here, as shown in FIG. 1, when the upper coil unit 700 is made flat, the lateral width dimension (the dimension in the x-direction) of a pair of the inner supports 20-1 is shorter than the lateral width dimension (the dimension in the x-direction) of the outer support 20-2. When the upper coil unit 700 is mounted on the bed coil unit 600, this size difference absorbs the difference in diameter between the inner side and the outer side, as well as reserving space between the inner support 20-1 and the outer support 20-2. Accordingly, work space for allowing the inner side support 20-1 to tightly adhere to the test object 103 is reserved, and the outer support 20-2 is placed being set apart from the test object 103 by a little distance. Therefore, even with a structure as covering the test object 103 entirely, it is possible to make the most of an advantage of the vertical magnetic field type MRI apparatus, that an oppressive feeling can be reduced.

The inner support 20-1 is made of a material having flexibility, and sufficient space is reserved inside the outer support 20-2, thereby allowing the inner support to tightly adhere to the test object 103 even when he or she is different in size to some extent.

In the present embodiment, the inner supports 20-1 and the outer support 20-2 are fixed to a pair of joining sections 710, and, therefore, can be easily attached to or detached from the bed coil unit 600 by attaching/detaching this pair of joining sections 710 to/from the pair of joint support parts 650. In addition, these three members are fixed to the pair of joining sections 710, and they can be treated as one thin member, as well as treated in the flat state and prepared for storage.

With reference to FIG. 2 to FIG. 29, a further detailed explanation will be made as to the MRI apparatus being provided with the receiver coil unit 500 according to the present embodiment.

Firstly, with reference to FIG. 2, a device configuration of the MRI apparatus will be explained specifically. FIG. 2 schematically illustrates a device block diagram of the MRI apparatus. This MRI apparatus comprises magnets 101 for generating a vertical static magnetic field, gradient magnetic field coils 102 for generating a gradient magnetic field, irradiation coils 107 for irradiating an RF pulse, a receiver coil 116 for receiving a nuclear magnetic resonance signal generated from the test object 103, a sequencer 104, and a computer 109, and the like. The irradiation coils 107 and the receiver coil 116 are installed within the magnet 101 and the gradient magnetic field generation coils 102.

The gradient magnetic field generation coil 102 is made up of gradient magnetic field coils having three axes being orthogonal to one another. Each of the triaxial gradient magnetic field coils is connected to a gradient power supply 105. The irradiation coil 107 is connected to an RF pulse generator 106 via an RF power amplifier 115. The sequencer 104 sends an instruction to the gradient power supply 105 and the RF pulse generator 106, so as to generate a gradient magnetic field and an RF pulse respectively from the gradient magnetic field coil 102 and the irradiation coil 107. The output from the RF pulse generator 106 is amplified by the RF power amplifier 115 and applied to the irradiation coil 107, thereby applying the RF pulse to the test object 103 via the irradiation coil 107.

A nuclear magnetic resonance signal generated from the subject 103 is received by the receiver coil 116. The receiver coil 116 is made up of multiple sub-coils 116-1 to 116-n. Details of the receiver coil 116 will be described below. After the signals received by the receiver coil 116 are amplified by the preamplifiers 117-1 to 117-n to a level necessary for detection, the receivers 108 subject the signals to A/D conversion (sampling) and detection. The center frequency (magnetic resonance frequency) as reference of the detection is set by the sequencer 104. The signal being detected is transferred to the computer 109, subjected to a re-sampling process, and then a signal processing such as an image reconstruction is performed. A result of the processing is displayed on the display 110.

As required, it is possible to store the signals and measurement conditions in the storage medium 111. When it is necessary to adjust the static magnetic field homogeneity, a shim coil 112 is employed. The shim coil 112 is made up of multiple channels, and current is supplied by a shim electric power supply 113. The sequencer 104 controls the current passing through each coil of the multiple channels, and generates an additional magnetic field from the shim coil 112 so as to correct the static magnetic field inhomogeneity. The sequencer 104 controls each device so as to operate at timing and with strength being programmed. Descriptions in these programs, particularly regarding application of the RF pulse, application of the gradient magnetic field, receiving timing of the nuclear magnetic resonance signal, and the strength of the RF pulse and gradient magnetic field are referred to as an imaging sequence.

With reference to FIG. 3 to FIG. 15, an explanation will made regarding a schematic outer structure and operational principle of the receiver coil employed in the MRI apparatus according to the present invention. In the following explanation, it is assumed that the static magnetic field direction (vertical direction) is z-direction, two directions orthogonal to the z-direction, also being orthogonal to each other, are x-direction and y-direction, a left-right direction of the subject 103 is x-direction, and the body axis direction is y-direction. FIG. 3 illustrates parts breakdown of the receiver coil unit.

Firstly, in FIG. 3 according to the present embodiment, the receiver coil unit 500 is placed in such a manner that three upper coil units 700a, 700b, and 700c are arranged along the y-direction, whereby the total body of the test object 103 can be covered. Here, one end of the inner support 20-1 in the y-direction extends farther than the end of the outer support 20-2 in the y-direction. When the upper coil units 700 are arranged in the y-direction, this extended part QQ is placed in such a manner as overlapping the inner support 20-1 of other upper coil unit 700 of the same sort.

The bed coil unit 600 is divided into three blocks Q1, Q2, and Q3 along the y-direction, and the coil arrangement within each of the three blocks is the same. Therefore, by connecting the upper coil units 700 respectively with the blocks, an area of the blocks as to which the connection is established can be subjected to an inspection. By way of example, the upper coil unit 700 is mounted on the block Q1 for an area in proximity to chest region, on the block Q2 for an area in proximity to lumbar region, and on the block Q3 for an area in proximity to legs region, thereby allowing an inspection of the area in the block on which the upper coil unit is installed. Accordingly, if the upper part coils unit 700 are installed on all of the three blocks, it is possible to inspect the total body of the test object 103.

In the present embodiment, it is possible to install a pillow member 510 on the receiver coil unit 500. Instead of the pillow member 510, a head-use receiver coil, not illustrated, may be installed.

Next, with reference to FIG. 4, a schematic structure of the receiver coil relating to the present embodiment will be explained. In the receiver coil according to the present embodiment has an arrangement in which five types of sub-coils are placed, each along the y-direction (the body axis direction of the subject), and it is configured such that the overall receiver coils cover almost the total body of the subject. FIG. 4 illustrates one block of the overall receiver coil covering the total body; the figure (A) is a perspective view, and the figures (B) to (D) are illustrations, respectively viewed from y-direction, z-direction, and x-direction. An actual receiver coil is used by dividing a coil conductor into multiple positions by a capacitor, thereby achieving a match between a resonance frequency of the coil and a nuclear magnetic resonance frequency. However, in the figures illustrating the present embodiment, the capacitor is omitted as appropriate.

As illustrated, the receiver coil according to the present embodiment incorporates a sub-coil 3-1 forming a current loop around the outer periphery of the subject 103, a sub-coil 4-1 forming two current loops through which current passes in the directions opposite to each other respectively on two planes placing therebetween the plane (x-z plane) on which the current loop of the sub-coil 3-1 is formed and which is located nearly equidistant from the two planes, sub-coils 5-1 disposed at the upper and lower parts (back side and ventral side) placing the subject 103 therebetween, sub-coils 6-1-1 and 6-1-2, and sub-coils 7-1-1 and 7-1-2 which are disposed in such a manner as covering the sides of the subject 103. The sub-coils 6-1-1 and 6-1-2, and the sub-coils 7-1-1 and 7-1-2 each uses two coils of the same type to constitute one block of the receiver coil. The five types of sub-coils are arranged in plane symmetry with respect to the plane (x-z plane) on which the current loop of the sub-coil 3-1 is formed. Using the block shown in FIG. 4 as a unit, multiple blocks can be arranged in the direction orthogonal to the plane, i.e., in the y-direction.

Next, specific configurations of the five-type sub-coils constituting the receiver coil and a relationship among these sub-coils will be described in detail.

The first type sub-coil 3-1 is a solenoid coil which is arranged around the outer periphery of the subject as shown in FIG. 5(A). As shown in FIG. 5(C), the y-axis sensitivity distribution 301 of the sub-coil 3-1 shows that there is a maximum value on the plane where the current loop exists, and since a high sensitivity area is large, it is also called as a large-FOV coil. Since the plane on which the current loop of the sub-coil 3-1 is formed serves as a reference for placing other type sub-coils, hereinafter, this plane is assumed as a reference plane of y=0. It is also assumed that the center of the current loop of the sub-coil 3-1 on the reference plane is an original point; x=0 and z=0. Although a single-turn solenoid coil is shown in FIG. 5(A), the number of turns may be more than one. By way of example, two-turn solenoid coil 3-2 may be applicable as shown in FIG. 5(B), and in this case, a central plane of the two-turn solenoid coil serves as the reference plane.

The second type sub-coil 4-1 is the sub-coil 4-1 which forms two current loops around the outer periphery of the subject as shown in FIG. 6(A). As shown in FIG. 6(B), the sub-coil 4-1 is a coil in which there are formed in the z-x plane, two current loops positioned symmetrically with respect to the reference plane of the sub-coil 3-1, and wire connection is established so that the current flows in the current loops, respectively in the directions opposite to each other. When the sub-coil 4-1 receives electric supply, the current passes through the two current loops, in the directions opposite to each other. Therefore, in proximity to the respective loops, strong magnetic fields may be generated by the current loops. However, as being apart from one loop, a component canceled by the magnetic field generated by the other loop increases, and in the midpoint between the two loops, the magnetic field becomes zero. In other words, as shown in FIG. 6(C), in the sensitivity distribution 401 on the y-axis of the coil 4-1, the sensitivity becomes approximately zero on the cross section (reference plane) on which the coil 3-1 exists, showing the sensitivity distribution being symmetrical about the cross section. It is to be noted that a magnetic field distribution actually generated when 1 W power is given to the feeding point, reverses in sign on the both sides about the point y=0, but in this example, an absolute value is taken to represent a sensitivity distribution curve (hereinafter, the sensitivity distribution curve is defined in the same manner).

With the arrangement as described above, the sub-coil 4-1 and the sub-coil 3-1 do not generate induced current mutually, and therefore, electromagnetic coupling between the sub-coil 3-1 and the sub-coil 4-1 is suppressed to a level which may cause no problem in practice. Therefore, combined sensitivity generated by the sub-coil 3-1 and the sub-coil 4-1 can be calculated by square-root of sum of squares of each sensitivity, and the distribution of the combined sensitivity is represented by the curve 901 as shown in FIG. 6(D). As illustrated, the sensitivity 901 in the case where the sub-coil 3-1 and the sub-coil 4-1 are combined becomes higher along the entire y-axis, than the sensitivity in the case where either of the sub-coil 3-1 and the sub-coil 4-1 is used.

The third type sub-coil 5-1 has a shape as shown in FIG. 7(A). As shown in FIG. 7(B), the sub-coil 5-1 comprises two coils 5-2 and 5-3 having approximately the same shape, being arranged in opposed manner in the front and rear of the subject 103 (z-axis direction), and the two coils are brought into conduction (connection) to achieve a coil having one feeding point 5-6. Each of the coils 5-2 and 5-3 has a shape including two current loops positioned side by side in y-direction, and there is formed a cross point between the two current loops. The cross points of the current loops of the respective two coils 5-2 and 5-3 are positioned in a plane where the current loop of the aforementioned sub-coil 3-1 exists, i.e., the reference plane, and the two coils 5-2 and 5-3 are arranged as being approximately symmetrical with respect to the subject 103.

With reference to FIG. 8, a magnetic field generated by the sub-coil 5-1 will be explained. FIG. 8(A) and FIG. 8(B) each illustrates the case where the coil 5-2 and the coil 5-3 are not brought into conduction. Firstly, as shown in FIG. 8(A), when the feeding is performed from each of the feeding points 5-7 and 5-8 so that current passes through in different directions (asymmetrically) in the coil 5-2 and the coil 5-3, that is, the feeding is performed so that the current passes through the coil conductive wires in the directions indicated by the arrows, the magnetic fields generated in the coil 5-2 are in the directions represented by the dashed arrows 8-1 and 8-2 in the figure, and the magnetic fields generated in the coil 5-3 are in the directions represented by the dashed arrows 8-3 and 8-4 in the figure. In the case above, inside the coil where the subject exists, both coils generate the magnetic fields directed to negative y-direction, thereby mutually reinforced.

On the other hand, as shown in FIG. 8(B), when the feeding is performed from each of the feeding points 5-7 and 5-8 so that current passes through in the same direction (symmetrically) in the coil 5-2 and the coil 5-3, that is, the feeding is performed so that the current passes through the coil conductive wires in the directions indicated by the arrows, the magnetic fields generated in the coil 5-2 are in the direction of the dashed arrows 8-5 and 8-6 in the figure, and the magnetic fields generated in the coil 5-3 are in the direction of the dashed arrows 8-7 and 8-8 in the figure. In the case above, in the area inside the coil where the subject exists, the magnetic fields being opposite to each other are generated on the y-axis, and at the point of z=0, the magnetic field is canceled mutually. Therefore, it would be understood that in the deep portion of the subject, the sensitivity becomes almost zero. It is to be noted that such generation of the magnetic fields is based on the premise that the currents passing through the conductive wire are in phase. It is further to be noted that coils having the same shape being opposed to each other may cause a coupling, and there is a possibility that deterioration of sensitivity is induced.

As shown in FIG. 8(C), the third type sub-coil 5-1 forms one coil by bringing the coil 5-2 and the coil 5-3 into conduction, and feeding is performed from the single feeding point 5-6. Then, the current passes through the coil conductive wire in the same manner as the case of FIG. 8(B). Specifically, the current is made to pass through the coil 5-2 and the coil 5-3, in the same directions at the positions being symmetrical with respect to the x-y plane where z=0. In this case, since there is conduction between the coil 5-2 and the coil 5-3, it is possible to allow the currents in phase to pass through the positions symmetrical with respect to the x-y plane. Consequently, the magnetic fields being generated are directed as indicated by the dashed arrows 8-9 to 8-12 as shown in the figure. When a distribution in the area within the coil where the subject exists is shown, as illustrated by the curve 501 shown in FIG. 8(D), there is obtained the distribution in which the magnetic field is zero on the x-y plane where z=0, and being asymmetrical with respect to the z-axis direction.

The fourth type sub-coil 6-1 is a coil (saddle coil) having two current loops which are arranged on the surface of the subject, as shown in FIG. 9(A). FIG. 9(A) illustrates only one piece of the fourth type coil. However, as shown in FIG. 9(B), two sub-coils 6-1-1 and 6-1-2 arranged in the y-axis direction may constitute one block of the receiver coil of the present embodiment. The two coils are arranged in such a manner that the plane (reference plane) where the aforementioned current loop of the first type sub-coil 3-1 is positioned in nearly the midsection between the two sub-coils. As an overall structure of the receiver coil, the sub-coils 6-1 are arranged continuously in the y-direction, thereby covering the subject entirely. On this occasion, the two coils adjacent to each other are arranged in such a manner as overlapping appropriately (around 10% of the area). With this configuration, magnetic coupling between the adjacent coils is removed. The sub-coil 6-1 has curved portions which surround the both side surfaces of the subject 103. FIG. 9(C) illustrates a sensitivity distribution in the x-axis direction of the sub-coil 6-1 which has the configuration as described above. As illustrated, the sub-coil 6-1 shows the sensitivity distribution 601 having high sensitivity in the deep portion of the subject, just like the sub-coil 3-1. Therefore, the sub-coil 6-1 is also referred to as a "large-FOV coil".

The fifth type sub-coil 7-1 is a coil having three current loops arranged on the surface on the subject as shown in FIG. 10(A), with curved portions surrounding the both side surfaces of the subject 103. FIG. 10(A) shows only one piece of the fifth type coil, but as shown in FIG. 10(B), two sub-coils 7-1-1 and 7-1-2 arranged in the y-axis direction may constitute one block of the receiver coil of the present embodiment. In one block, the two sub-coils 7-1-1 and 7-1-2 are arranged in such a manner that a reference plane (the plane where the current loop of the first type sub-coil 3-1 is formed) is positioned in nearly a midpoint in the y-axis direction between the two sub-coils. As an overall structure of the receiver coil, the sub-coils 7-1 are arranged continuously in the y-direction, thereby covering the subject entirely. Also in the case of the fifth type sub-coil, the two coils adjacent to each other are arranged in such a manner as overlapping appropriately (around 10% of the area), and with this configuration, magnetic coupling between the adjacent coils is removed.

In the sub-coil 701 having the configuration described above, the current in the same direction is passing through the two conductive wires which cross each other at the two cross points. Therefore, the sensitivity at the cross points is the highest. Since the direction of the current on one cross point is opposite to the current on the other cross point, the sensitivity becomes the minimum on the perpendicular bisector of the line which connects the two cross points, whereas the sensitivity at the cross points is the maximum. The sensitivity distribution of this sub-coil 7-1 is represented by the curve 701 in FIG. 9(C). As illustrated, two regions (regions where the two cross points exist) showing the maximum sensitivity by the coil 7-1 having three current loops are arranged in such a manner that the two regions approximately coincide with around the positions of two regions where the sub-coil 6-1 having two current loops show the minimum sensitivity. Accordingly, when the current passes through one coil, it is possible to assume that the induced magnetic field generated in the other coil is ignorable practically, and the electromagnetic coupling between the sub-coil 6-1 and the sub-coil 7-1 can be reduced to a level which may cause no problem in practice.

Next, an explanation will be made regarding the relationship between sub-coils from the first type to the fifth type, particularly as to the sensitivity distribution direction and the electromagnetic coupling of each sub-coil.

It has been explained that the electromagnetic coupling between the sub-coil 3-1 and the sub-coil 4-1 which are arranged around the outer periphery of the subject is suppressed to a level which causes practically no problem, and that the electromagnetic coupling between the sub-coil 6-1 and the sub-coil 7-1 is also suppressed to a level which causes no problem practically, according to an appropriate arrangement.

Here, the relationship between the sub-coils 3-1 and 4-1 and the sub-coils 6-1 and 7-1 will be considered. The sub-coil 3-1 and the sub-coil 4-1 arranged around the outer periphery of the subject show the maximum sensitivity in the y-axis direction. On the other hand, the sub-coil 6-1 and the sub-coil 7-1 arranged in proximity to the subject show the maximum sensitivity in the x-axis direction. Therefore, when the sub-coil 3-1 and the sub-coil 6-1 are arranged as shown in FIG. 11(A) for example, these coils are electrically orthogonal to each other, and the electromagnetic coupling can be suppressed to a level which causes no problem practically. In addition, since the sub-coil 3-1 and the sub-coil 6-1 have high sensitivity at the deep portion of the subject, it is expected that the sensitivity in the deep portion of the subject can be further enhanced with the arrangement as described above. The maximum sensitivity direction of the sub-coil 4-1 is also in the y-axis direction. Therefore, as shown in FIG. 11(B), if the coil 6-1 is shifted from a position where the coil 3-1 exists, to a position where the coil 4-1 exists, to make an arrangement like the coils 6-1-1 and 6-1-2, an effect of further enhancement in sensitivity can be expected in the deep portion of the subject without generating the coupling, just like the case above.

In the similar manner, the sub-coil 7-1 is also electrically orthogonal to the sub-coil 3-1 and the sub-coil 4-1, and the electromagnetic coupling with the sub-coil 3-1 and the sub-coil 4-1 can be suppressed to the level which causes no problem practically. Therefore, even though any of the sub-coils 6-1-1 and 6-1-2, and the sub-coils 7-1-1 and 7-1-2, being continuously arranged in the y-axis direction, are made to overlap in proximity to the plane including the sub-coil 3-1 or the sub-coil 4-1, it is possible to suppress the electromagnetic coupling to a level which causes no problem practically.

As thus described, as for the first type sub-coil 3-1, the second type sub-coil 4-1, the fourth type sub-coil 6-1, and the fifth type sub-coil 7-1, if an appropriate relationship is established in the arrangement thereof as described above, together with utilizing a method of overlapping, the electromagnetic coupling can be removed. If required, it is possible to use at the same time, a publicly known decoupling method, for example, a method for suppressing a magnetic coupling by using an amplifier having low-input impedance for signal detection.

Moreover, by using the orthogonality between the sub-coils 3-1 and 4-1, and the sub-coil 6-1, the sensitivity in the deep portion of the subject can be enhanced. FIG. 11(C) shows the y-axis direction sensitivity distribution in the deep portion of the subject. The curves 301 and 401 respectively represent the y-axis direction sensitivity distribution of the sub-coil 3-1 and the sub-coil 4-1, which are the same as the curves shown in FIG. 6(C). The curves 602 and 603 respectively represent the y-axis direction sensitivity distribution of the sub-coil 6-1-1 and the sub-coil 6-1-2 shown in FIG. 9(C). The curve 801 indicates the y-axis direction sensitivity distribution in the case where the sub-coil 3-1 and sub-coils 6-1-1 and 6-1-2 are combined for QD to enhance the sensitivity. The curve 902 indicates the sensitivity distribution in the case where the sensitivity of the sub-coil 4-1 is further combined. It would be understood that by using the first type, the second type, the fourth type, and the fifth type coils, it is possible to enhance the y-axis direction sensitivity across a wide area.

Then, an explanation will be made regarding a relationship of the third type sub-coil 5-1 with the first type and the second type sub-coils 3-1, 4-1 whose maximum sensitivity is shown in the y-axis direction, and with the fourth type and the fifth type sub-coils 6-1 and 7-1 whose maximum sensitivity is shown in the x-axis direction. FIG. 12 shows an arrangement of the sub-coil 3-1, the sub-coil 5-1, and the sub-coil 6-1, which constitute one block of the receiver coil.

As already described, the third type sub-coil 5-1 is a coil in which the coils 5-2 and 5-3 of the same shape each having two current loops with one cross point, are arranged in symmetrical with respect to a plane (x-y plane) 1000 being perpendicular to the static magnetic field, and conduction is established between the two coils. The current loops are positioned mostly on the planes 1002 and 1003 (backside and ventral side of the subject) in parallel with the plane 1000. The cross points 5-4 and 5-5 of the coils are arranged so that they are positioned within the plane 1001 in which the current loop of the first type sub-coil 3-1 is formed, i.e., the plane including an axis substantially parallel with the static magnetic field.

With the configuration above, in the sub-coil 5-1, there exist current loops at symmetrical positions, through which current passes in the directions opposite to each other, in any planes including the plane (x-y plane) 1000 perpendicular to the static magnetic field, and the planes (z-x plane 1001, where y=0 or y-z plane where x=0) passing through the original point and parallel with the static magnetic field. Therefore, as described below, it is possible to remove electromagnetic coupling with other sub-coils. It is further possible to improve G factor, in the combination with other sub-coils.

Firstly, with reference to FIG. 13(A), a relationship with the first type sub-coil 3-1 will be explained. FIG. 13(A) is a schematic illustration in the case where the first type sub-coil 3-1 and the third type sub-coil 5-1 are placed according to the arrangement method as described above, and directions of current passing through these sub-coils are also illustrated. When feeding is performed to the sub-coil 3-1, the current passes through the current loops of the sub-coil 3-1, in the directions as indicated by the arrows in the figure. As is known from the figure, even though induced current may pass through the loop of the sub-coil 5-1 at a part in proximity to the loop of the sub-coil 3-1, there exist on the sub-coil 5-1, current loops through which current passes in the directions definitely opposite to each other, at symmetric positions with respect to the plane (x-y plane where z=0) 1000 passing through the original point and perpendicular to the static magnetic field, or with respect to the planes (z-x plane 1001 where y=0, or y-z plane where x=0) passing through the original point and parallel with the static magnetic field. Consequently, there is no induced current passage being generated. On the other hand, if feeding is performed to the sub-coil 5-1, the current passes through the sub-coil 5-1 in the directions as indicated by the arrows in the figure, but just like the case where the feeding is performed to the sub-coil 3-1, no induced current passage occurs in the sub-coil 3-1.

Next, with reference to FIG. 13(B), a relationship with the second sub-coil 4-1 will be explained. FIG. 13(B) is a schematic illustration in the case where the second type sub-coil 4-1 and the third type sub-coil 5-1 are placed according to the arrangement method as described above, and directions of current passing through these sub-coils are also illustrated. Here, it is assumed that when feeding is performed to the sub-coil 4-1, the current passes through the current loops of the sub-coil 4-1, in the directions as indicated by the arrows in the figure. Just like the case of FIG. 13(A), even through induced current may pass through the loop of the sub-coil 5-1 at apart in proximity to the loop of the sub-coil 4-1, there exist on the sub-coil 5-1, current loops through which current passes in the directions definitely opposite to each other, at symmetric positions with respect to the plane (x-y plane where z=0) 1000 passing through the original point and perpendicular to the static magnetic field, or with respect to the plane (z-x plane 1001 where y=0, or y-z plane where x=0) passing through the original point and parallel with the static magnetic field. Consequently, there is no induced current passage. If feeding is performed to the sub-coil 5-1, the current passes through the sub-coil 5-1 in the directions as indicated by the arrows in the figure, but no induced current passage occurs in the sub-coil 4-1, just like the case where feeding is performed to the sub-coil 4-1.

As for the fourth type sub-coil 6-1 and the fifth type sub-coil 7-1, which has the maximum sensitivity in the x-axis direction, the coupling can be suppressed to the level which causes no problem in a similar manner. Also in the case where the sub-coils 5-1 are arranged continuously in the y-direction, the electromagnetic coupling between the adjacent coils can be eliminated by overlapping the sub-coils appropriately one another (around 10% of the area).

In the receiver coil according to the present embodiment, the electromagnetic coupling in each of the five types of sub-coils can be suppressed. Therefore, it is possible to eliminate the use of an auxiliary coil or the like for removing the electromagnetic coupling, or it is possible to minimize the use thereof, thereby restricting the increase of the number of channels. Assuming a combination of five types of sub-coils as one block, multiple sub-coils can be placed side by side in the body axis direction of the subject, and it is possible to perform imaging of a wide area such as a total body, keeping high sensitivity in the deep portion of the subject.

As shown in FIG. 6(C), FIG. 8(D), and FIG. 9(C), there exists a combination of sub-coils having sensitivity directions different respectively in the x-axis direction, y-direction, and z-direction. Therefore, whichever direction is selected as the phase encoding direction, it is possible to achieve small G factor, and even when parallel imaging is applied, a favorable image can be obtained. In particular, in an imaging plane where the first type coil being a large FOV coil exists, the G factor can be made small whichever direction is selected as the phase encoding direction.

As for the G factor, if the increase in the number of channels is allowed, there is an improvement effect. However, if the receiver coil for imaging a total body is implemented, by placing the receiver coil being made up of the sub-coils of 8 channels for one block, for instance, along the body axis direction of the subject, the increase in the number of channels is undesirable as a matter of course. Due to a restriction in fabrication precision, it is difficult that the positions of the cross points 5-4 and 5-5 exactly coincide with the current loop plane 1001 of the large FOV coil 3-1. However, it is preferable that this coincidence is achieved with an error within around 20% with respect to the length of the coil 5-1 in the y-axis direction. Even though around 20% of displacement occurs in the length of the coil 5-1 in the y-direction due to the restriction in implementation, an improvement effect of the G factor can be expected.

An explanation has been made as to an arrangement of one block of the receiver coil according to the present embodiment. Next, an explanation will be made as to a configuration of the receiver coil, in which the aforementioned five types of sub-coils are continuously arranged in the body axis direction (y-direction in this example) of the subject to cover his or her total body. FIG. 14 and FIG. 15 illustrate examples where the five types of sub-coils are arranged continuously. FIG. 14 is x-y plan view, viewed from the z-axis direction, and FIG. 15 is y-z plane view, viewed from the x-axis direction. In each of FIG. 14 and FIG. 15, figure (A) illustrates a method for arranging the sub-coils 3-1 and the sub-coils 4-1, figure (B) illustrates a method for arranging the sub-coils 5-1, figure (C) illustrates a method for arranging the sub-coils 6-1, and figure (D) illustrates a method for arranging the sub-coils 7-1, and each of the methods are shown independently for facilitating visualization. In each of the figures, one block surrounded by the dotted line is assumed as a common block, and each of the sub-coils is arranged to have the positional relationship with respect to the subject 103 within the same block, as shown in FIG. 4.

In view of the y-axis direction, as illustrated in (B), (C), and (D) of FIG. 14 and FIG. 15, the sub-coils 5-1, 6-1, and 7-1 have the approximately the same length in the y-axis direction, and the adjacent sub-coils overlap one another by an appropriate area, thereby achieving a continuous arrangement. In particular, as for the sub-coil 6-1, the sensitivity in the deep portion of the subject is improved together with the sub-coil 3-1 and the sub-coil 4-1, and by the overlaps between the adjacent sub-coils, it is possible to keep a constantly high sensitivity in the y-direction. In addition, if the sub-coil 3-1 and the sub-coil 4-1 as shown in (A) are made to operate as they are illustrated, the electromagnetic coupling is extremely large between the adjacent coils, and this magnetic coupling cannot be suppressed sufficiently even with a publicly known method (for example, a method for suppressing the magnetic coupling by using an amplifier with a low-input impedance for detecting signals). Therefore, it is configured such that one sub-coil 3-1 and one sub-coil 4-1 exist in one imaging block. The sub-coils 4-1-1 and 4-1-2 which are combined with two sub-coils 3-1, e.g., sub-coils 3-1-1 and 3-1-2, may share a conductor part which is placed between the sub-coils 3-1-1 and 3-1-2. Details of this configuration will be described later, along with the control of sub-coils of the receiver coil according to the present embodiment.

Next, with reference to FIG. 16 to FIG. 23, further detailed explanation will be made regarding an external structure of the receiver coil unit 500 used for a total body, incorporating the receiver coils described above. FIG. 16 illustrates external perspective views of the receiver coil unit, (A) is an external view of the receiver coil unit, and (B) is an external perspective view in the state where a test object is placed inside. FIG. 17 is a structural illustration of the bed coil unit, (A) illustrates parts breakdown of the bed coil unit, and (B) is an external view of the joint support part and the joint part. FIG. 18 is an external view of the upper coil unit in the state of being set. FIG. 19 is an external perspective view of the inner support. FIG. 20 is an external view of the upper coil unit folded flat. FIG. 21 and FIG. 22 are illustrations to explain other embodiment when a different sized upper coil unit is installed; FIG. 21 illustrates examples of a swing-type joint structure; (A) is a front view when a standard sized upper coil unit is installed, and (B) is a front view when a large sized upper coil unit is installed, and FIG. 21 is a front view in which the joint support parts are provided in two rows. FIG. 23 is a partial perspective view showing a method how to install a free end part of the inner support.

Firstly, in FIG. 16, in the present embodiment, there is formed an open part 602 for placing a head region of the test object 103, on one end of the longitudinal direction (y direction) of the bed coil unit 600. In the present embodiment, since the total body, lower from the arm part, is available for inspection, the test object 103 as a target for the inspection opens the arms toward both sides, and inserts the body lower from the arm part into the upper coil unit 700.

When the upper part coil unit 700 is installed continuously in the y-direction, the joint support parts 650 are placed in a row spaced by a predetermined distance, in order that the first type sub-coils, the second type sub-coils, and the like, described above are positioned to have an appropriate spacing. In the present embodiment, the three upper coil units 700 an extending portion QQ at one end of the inner support 20-1 in the y-direction is placed in such a manner as overlapping the inner support 20-1 of other upper coil unit 700 of the same sort.

In FIG. 17(A), the bed coil unit 600 of the present embodiment incorporates, for example, a lower case 620 being open-topped, an upper case 621 in a concave shape covering the top of the lower case 620, a mat part 622 constituting an installation surface 601 in the center of the concave portion of the upper case 621. There are formed mounting openings 624 for mounting multiple joint support parts 650, on rims 623 formed in elongated manner overhanging from the both sides (both ends in the x-direction) of the upper case 621.

There is formed a coil accommodation space 625 between the upper case 621 and the lower case 620, the space being continuous from the lower space of the rims 623. This coil accommodation space 625 contains an arrangement of coils which are connected with the multiple joint support parts 650 placed on the pair of rims 623.

In FIG. 17(B), the joint support part 650 is made up of a box-shaped main body 651 and a flange part 652 extending outwardly around the main body. There are formed multiple coil mounting support parts 653 on the upper surface of the main body 651. The flange part 652 has screw holes in the longitudinal direction thereof, and the flange part 652 is screwed on the mounting opening 624 via the screw holes. When this screwing is performed, the joint support part 650 is not fastened securely to the mounting opening 624, but it is screwed with a little "wobbling" to provide movability in the y-direction and the x-direction. Installation of the joint support part 650 in such a manner as described above may facilitate putting on and taking off the upper coil unit 700 more easily than being fastened securely.

In detail, in the present embodiment, the test object 103 is placed on his or her back on the bed coil unit 600, then one joining section 710 of the upper coil unit 700 is coupled, and thereafter, the other joining section 710 is coupled with the joint support part 650. On this occasion, since the joining section 710 is provided with five joint parts 770 in a line, alignment (positioning) becomes difficult if the five joint support parts 650 arranged in a line as the counterpart are fixed without any flexibility. Considering this point, in the present embodiment, the five joint support parts 650 are installed in such a manner that each has a free play, and therefore this facilitates coupling.

On the other hand, the joint part 770, more one of them being mounted on the joining section 710 of the upper coil unit 700, is provided with multiple coil projections 772 on one surface of the box shaped main body 771, at the positions to fit into the coil mounting support parts 653. These coil projections 772 are inserted into the coil mount support parts 653 and fit therein, thereby coupling the coils of the upper coil unit 700 and the coils of the bed coil unit 600. The other end of the coil projection 772 are connected to the coils of the upper coil unit 700.

Next, with reference to FIG. 18 to FIG. 20, an external structure of the upper coil unit 700 will be further explained. In FIG. 18, on the upper surface of the joining section 710 formed in a stick-like shape, there is formed a concave shaped attaching portion 711 in which the inner support 20-1 and the outer support 20-2 are inserted for installation. The inner support 20-1 and the outer support 20-2 are superimposed one on another so that the former is positioned inside and the latter outside, and inserted into the attaching portion 711 and installed via an adhesive agent or screws. On the other hand, on the lower surface of the joining section 710 formed in stick-like shape, there are arranged the multiple joint parts 770 along the longitudinal direction thereof.

FIG. 19 is an external perspective view of the inner support 20-1 in the state where the outer support 20-2 and the joining section 710 are removed. In FIG. 19, the inner support 20-1 according to the present embodiment has two openings 550$a$ and 550$b$ formed side by side in the y-direction. Accordingly, a planar frame 551 large in width is formed around the openings, and coils are arranged within this planar frame 551. In addition, one end in the y-direction of the planar frame 551 is formed in such a manner as extending in the y-direction farther than the end P of the joining section 710.

Next, FIG. 20 is an external perspective view showing the upper coil unit 700 being folded flat. In FIG. 20, the outer support 20-2 has a thin plate-like shape, being a rectangular shape having a length in the x-direction longer than the length in the y-direction. In this outer support 20-2, there are formed in the y-direction a plurality of openings 550 being long in the x-direction, and at the center in the x-direction, the opening 550 is divided into left and right in the x-direction by the central crosspiece 552 which is formed along the y-direction. The outer support 20-2 according to the present embodiment is provided with a planar frame 553 formed in a shape of grating in such a manner as surrounding eight openings 550, which are arranged in two rows on the both sides of the central crosspiece 552 and in four rows in the y-direction, and coils are arranged in this planar frame 553.

Next, with reference to FIG. 21 and FIG. 22, an embodiment will be explained, which treats the test objects 103 being different in size in the x-direction. In the foregoing embodiment, there is reserved space formed between the inner support 20-1 and the outer support 20-2, and therefore it is adaptable to a test object 103 who is large in width to some extent. However, if the test object 103 is much larger in width (a fat person and the like), it is difficult for one-size receiver coil unit 500 to cope with such test object. It is also difficult from viewpoints of economical aspect and installation site, to hold more than one bed coil units 600 having different sizes in width (width in the x-direction).

In view of the problem above, in another embodiment, multiple upper coil units 700 having different sizes in width (width in the x-direction) are prepared. With a contrivance to a method how to install such multiple upper coil units 700 to the bed coil unit 600, one bed coil unit 600 is allowed to perform inspection of the test object 103 having different width (width in the x-direction).

The embodiment shown in FIG. 21 illustrates an example in which the joint support part 650 of the bed coil unit 600 is installed swingably. FIG. 21(A) illustrates a state where a standard upper coil unit 700 is mounted on the bed coil unit 600, and FIG. 21(B) illustrates a state where one-size larger upper coil unit 700a is mounted on the bed coil unit 600. In this embodiment, the joint parts 770a provided on both ends in the x-direction, in such a manner as swingable, so that the tops of the joint parts are opened toward both sides (in the x-direction) respectively, about the rotation axis on the bottom end. With this configuration, when the large upper coil unit 700a being long in the x-direction is installed, the joint parts 770a are opened toward both sides (x-direction), and a length in the x-direction between the pair of the joint parts 770a expands from L1 to L2. Therefore, it is possible to place inside test object 103 who is one-size larger, than the case where the standard sized upper coil unit 700 is used.

According to yet another embodiment as shown in FIG. 22, there are provided two rows of joint support parts 650 and 650b on each of both sides in the x-direction. The standard upper coil unit 700 is coupled with the inner joint support part 650, and the one-size larger upper coil unit 700a is installed on the outer joint support part 650b. With this configuration, an operational effect similar to the embodiment shown in FIG. 21 can be achieved.

Next, with reference to FIG. 23, a stopper 70 will be explained, which is used for fixing the free ends of the inner support 20-1. FIG. 23 is a partial perspective view showing the inner support. In FIG. 23, according the present embodiment, the ends on the center side (in the x-direction) of the inner support 20-1, serve as the free ends. Therefore, the inner support is opened or closed in the midsection of the test object 103, and the test object 103 is covered by a pair of the inner supports 20-1 in such a manner as tightly adhering thereto. The free ends of the inner support 20-1 can be opened and closed by using various kinds of stopper 70. However, since the inner support 20-1 is located inside the outer support 20-2 in a grating shape, a contrivance is needed to take usability a step further.

In the present embodiment, ring-shaped stoppers 70 are provided respectively on the fixed end and the free end of the inner support 20-1. A string 71 is made to pass through the ring-like stoppers, and by fastening the string, the string 71 is allowed to press the inner support 20-1 from the outside. Pairs of the stoppers 70, which are provided respectively on the fixed end and on the free end of the inner support 20-1, are placed appropriately along the y-direction, and they are connected via the string 71. Accordingly, the overall inner support 20-1 is made to tightly adhere to the test object 103 to wrap it around.

Next, with reference to FIG. 24 to FIG. 26, a control method will be explained in the case where the aforementioned total-body use receiver coil is applied to a total-body imaging. Typically, in the total-body imaging, the imaging is performed by dividing the imaging area into multiple blocks in the body-axis direction of the subject (in the y-direction in a vertical magnetic field MRI). Also in the MRI apparatus according to the present embodiment, it is controlled so that switching takes place in the total-body use receiver coil, whereby only a sub-coil which includes an imaging block is allowed to operate.

FIG. 24 illustrates configuration examples of the sub-coil 3-1 and the sub-coil 4-1, each provided with a switching circuit. FIG. 24(A) illustrates the sub-coil 4-1 (4-1-1 and 4-1-2) corresponding to two blocks. A current loop positioned at the center, among the three current loops surrounding the outer periphery of the subject 103, is shared by the two sub-coils 4-1-1 and 4-1-2. In the figure, the left current loop and the center current loop constitute the sub-coil 4-1-1, and the right current loop and the center current loop constitute the sub-coil 4-1-2. The feeding parts 20-1 and 20-2 are respectively connected to preamplifiers not illustrated. When a nuclear magnetic resonance signal is received from the subject, it is amplified by the preamplifier, subjected to a signal processing after detection and AD conversion. In addition, a capacitance 19-1 (from 19-1-1 to 19-1-5) are connected respectively to the current loops and junctions of the current loops, in parallel with the current loops, and constitute loop circuits together with inductances 19-2 (from 19-2-1 to 19-2-5). Values of the capacitance 19-1 and the inductance 19-2 are adjusted so that resonance occurs in the loop circuit at the resonance frequency. In addition, the loop circuits are respectively provided with switching circuits 19-3 (from 19-2-1 to 19-3-5) to make the current loop in non-operating state.

With this configuration, when direct current passes through the switching circuits 19-3 of the sub-coil 4-1, the switching circuit becomes conductive, and the loop circuit forms a resonance circuit. This is equivalent to the condition that a high-resistance device is inserted in the capacitance 19-1, and an RF current does not pass any more through the sub-coil 4-1 itself. That is, the nuclear magnetic resonance signals generated from the subject are not received. On the other hand, the switching circuit 19-3 into which the direct current does not pass is in open-state, the capacitance 19-1 and the inductance 19-2 connected in parallel with the sub-coil 4-1 do not form the loop circuit, and the sub-coil 4-1 and the capacitance 19-1 form the RF receiver coil. That is, the nuclear magnetic resonance signals generated from the subject are received. By way of example, if it is controlled so that direct current does not pass through the switching circuits 19-3-1, 19-3-2, and 19-3-4, whereas it passes through the switching circuits 19-3-3 and 19-3-5, the sub-coil 4-1-1 is allowed to operate as the receiver coil, but the sub-coil 4-1-2 is not allowed to operate as the receiver coil. That is, any electromagnetic coupling does not occur between the sub-coils 4-1-1 and 4-1-2.

In the similar manner, as for the sub-coil 3-1 as shown in FIG. 24(B), for example, if it is controlled so that direct current does not pass through the switching circuit 19-3-6, whereas it passes through the switching circuit 19-3-7, the sub-coil 3-1-1 is allowed to operate as the receiver coil, but the sub-coil 3-1-2 is not allowed to operate as the receiver coil. Furthermore, though not illustrated, at least one switching circuit 19-3, capacitance 19-1, and inductance 19-2 may be provided for each loop of other types of sub-coils 5-1, 6-1, and 7-1. For example, if it is controlled so that the direct current passes through the switching circuit at the time of RF irradiation, it is possible to prevent a breakdown of the coil and the receiving system circuit due to the RF irradiation, and at the same time, a transmit-receive coupling can be prevented.

When the total-body use receiver coil as shown in FIG. 14 and FIG. 15 is employed, it is preferable that one sub-coil 3-1 and one sub-coil 4-1 are activated, according to the inspection area, and two of each of the sub-coils 5-1, 6-1, and 7-1 are activated according to the area, whereby eight channels in total are activated, and other sub-coils are rendered to be in non-operating state.

FIG. 25 illustrates a configuration example of a control system of the receiver coil. FIG. 25 shows only the sub-coil 3-1 as a representative example of the receiver coil. However, other types of sub-coils may be configured in the same manner. This control system incorporates mainly a selection circuit 19-4 for selectively connecting the sub-coil to a detection circuit 19-5, a DC power switching unit 19-6 for switching a control signal to the switching circuit 19-3 provided for each of the sub-coils, and a control unit 19-7.

The selection circuit 19-4 is connected between a preamplifier, which is connected to a feeding point of the sub-coil, and the detection circuit 19-5. When a signal 2001 corresponding to the inspection area is transmitted from the control unit 19-7, the selection circuit selectively connects the sub-coil existing in the inspection area with the detection circuit 19-5, in response to the signal. When a control signal 2002 corresponding to the inspection area is transmitted from the control unit 19-7, the DC power switching unit 19-6 is controlled so that direct current passes through the switching circuit 19-3 of the sub-coil in the non-operating state, in response to the signal. The control unit 19-7 preferably transmits the control signal 2001 for selecting an operating coil by the selection circuit 19-4, in sync with the control signal 2002 for the power switching circuit 19-6. By way of example, a position detecting means is provided on a moving bed or table, and a trigger signal 2003 in accordance with the position of the bed or the table may be passed to the control means 19-7 for performing the control.

With the configuration as described above, the sub-coil being in the operating state receives a nuclear magnetic resonance signal from the subject, and this nuclear magnetic resonance signal is amplified by the preamplifier connected to the feeding point, and then sent to the detection circuit 19-5. On this occasion, a received wave from the coil other than the imaging area is not sent to the detection circuit. Received signals from multiple sub-coils can be simultaneously processed by one detection circuit.

Next, an explanation will be made as to a specific example of coil control, when imaging is performed by using the receiver coil of the present embodiment, while moving a table on which a subject is placed. In the moving table imaging by using the receiver coil of the present embodiment, an operating state of each sub-coil is selectively switched according to the inspection area. One example of operation time chart of each of the coils is shown in FIG. 26. FIG. 26 illustrates a timing chart in which the imaging area is divided into seven regions from (1) to (7), and imaging is performed by changing the imaging area sequentially from (1) to (7). Timings of rise and fall in the timing chart are synchronized with a trigger signal which is issued when the position detection means installed on the moving table detects a position, each indicated by the dotted line.

By way of example, an explanation will be made as to a case where imaging of the imaging area (1) is finished, going through the imaging area (2), and the imaging of the imaging area (3) is performed. While the imaging area (1) is imaged, the sub-coils 3-1-1, 4-1-1, 5-1-1, 5-1-2, 6-1-1, 6-1-2, 7-1-1 and 7-1-2 are operating. When the position detection means provided on the moving table detects a border line (dotted line z3 in the figure) between the imaging area (1) and the imaging area (2), at the timing of the dotted line t3, the sub-coils 3-1-1 and 4-1-1 become in the state of non-operating, and simultaneously the sub-coil 3-1-2 and the sub-coil 4-1-2 become in the state of operating. While the imaging of the imaging area (2) is performed, when the position detection means detects around the center of the imaging area (2) (dotted line z4 in the figure), at the timing of the dotted line t4, the sub-coils 5-1-1 becomes in the state of non-operating, and simultaneously the sub-coil 5-1-3 becomes in the state of operating. Furthermore, when the position detection means detects a border line (dotted line z5 in the figure) between the imaging area (2) and the imaging area (3), at the timing of the dotted line t5, the sub-coils 6-1-1 and 7-1-1 become in the state of non-operating, and simultaneously the sub-coil 6-1-3 and the sub-coil 7-1-3 become in the state of operating. Hereinafter, when the position detection means detects the z coordinate indicated by the dotted lines, each sub-coil switches simultaneously the state of operating/non-operating at each time indicated in the timing chart as shown in FIG. 26. It is to be noted that the way how to divide the imaging area and the timing are not limited to the example as illustrated, and they may be configured optionally.

Regarding the total-body use receiver coil which combines sub-coils from the first type to the fifth type according to the present embodiment, there have been explained the structure of sub-coils constituting one block, the arrangement thereof, the structure to achieve a total-body coil, the control method, and the like. However, a basic feature of the receiver coil according to the present invention is a combination of the first sub-coil (sub-coil 3-1) forming the current loop around the outer periphery of the subject, and the second sub-coil (sub-coil 5-1) having two cross points which are positioned at the current loop plane (reference plane) of the first coil, with the current passage directions being symmetrical with respect to the plane crossing the reference plane. This arrangement of these coils enables a parallel arrangement of multiple coils, and also enables a combination with other sub-coils, while suppressing increase in the electromagnetic coupling and/or in the number of channels. Therefore, the receiver coil according to the present embodiment may be variously modified on the basis of the combination of the aforementioned first sub-coil and the second sub-coil in a predetermined arrangement. For example, there is another embodiment in which the sub-coils 4-1, 6-1, and 7-1 explained in the aforementioned embodiments are not included. In the similar manner, a configuration of only one block may be included. Furthermore, it is a matter of course that a coil shape may be transformed in accordance with the inspection object within the scope of the arrangement described above.

In order to validate the effect of the receiver coil according to the present embodiment, a G-factor was obtained by performing a simulation as to multiple sub-coils, assuming various directions as phase encoding directions. With reference to FIG. 27 to FIG. 29, results will be explained next.

EXAMPLE

Firstly, an arrangement plan of the sub-coils, with which the simulation was performed, and the resulted G-factor are shown in FIG. 27. FIG. 27(A) shows an arrangement plan of the sub-coils on the y-z plane viewed from the x-axis direction and FIG. 27(B) shows an arrangement plan of the sub-coils on the x-y plane viewed from the z-axis direction. The sub-coils 3-1 and 4-1 were identical to the sub-coils with the same numbers in the receiver coil as shown in FIG. 4. The sub-coils 6-1-1 and 6-1-2 were obtained by optimally transforming the conventional large FOV coil 6-1 (a saddle coil, in this example), and arranged with appropriate overlaps. The sub-coils 7-1-1 and 7-1-2 were obtained by optimally transforming the sub-coil 7-1 which provided a sensitivity distribution in the left-right direction of the subject (hereinafter, referred to as "RL direction", and it is x-direction in this example), and arranged with appropriate overlaps. The sub-coils 5-1-1 and 5-1-2 were obtained by arranging two sub-coils 5-1 in such a manner that they overlapped one another appropriately, and also the cross points 5-4 and 5-5 of the sub-coils 5-1 existed on the same cross section 1001 where the sub-coil 3-1 existed. In FIG. 27(A) and FIG. 27(B), the reference numerals 1001 and 1004 indicate the planes (z-x planes) on which the loop surfaces of the sub-coils 3-1 and 4-1 existed respectively.

FIG. 27(C) and FIG. 27(D) show the G-factor, as a result of the simulation respectively on the cross sections 1001 and 1004, in the case where the front-rear direction of the subject was selected as the phase encoding direction (a direction connecting the backside and ventral side, hereinafter referred to as "AP direction") (here, it corresponds to z-direction). These figures represented values of each pixel two-dimensionally, obtained from the sensitivity distribution of each sub-coil, which were calculated according to the formula disclosed by the non patent document 2. In a similar manner, FIG. 27(E) and FIG. 27(F) show the G-factor as a result of the simulation respectively on the planes 1001 and 1004 in the case where the RL direction was selected as the phase encoding direction. As discussed, the G-factor is a value at least 1, and it is an index value indicating that as the value becomes closer to 1, the sub-coil arrangement is assumed to be more ideal. In the figure, as the G-factor approaches 1, it is expressed in blacker color, and as the G-factor becomes a larger value, it is expressed in whiter color. As is shown, in the receiver coil of the present embodiment, the G-factor map was expressed almost in black within the subject existence area (indicated by dotted line in the figure), and it was found that the arrangement of sub-coils was favorable.

Comparative Example 1

As a comparative example, a simulation of the G-factor was performed by using a receiver coil made up of a combination of sub-coils, in which sub-coils corresponding to the sub-coils 5-1-1 and 5-1-2 of the above embodiment were not included. FIG. 28 illustrates an arrangement plan of the sub-coils and the G-factor as a result. Also in FIG. 28, FIG. 28(A) shows an arrangement plan of the sub-coils on the y-z plane viewed from the x-axis direction, and FIG. 28(B) shows an arrangement plan of the sub-coils on the x-y plane viewed from the z-axis direction. The sub-coils 3-1 and 4-1 were identical to the sub-coils with the same numbers in the receiver coil as shown in FIG. 4. The sub-coils 6-2-1, 6-2-2, 6-3-1, and 6-3-2 were surface coils (for example, 8-shaped, butterfly type coils), and the sub-coils 7-2-1, 7-2-2, 7-3-1, and 7-3-2 were obtained by appropriately transforming the sub-coil 7-1 which provided a sensitivity distribution in the RL direction. These sub-coils were made to overlap one on another appropriately, so as to make the electromagnetic coupling smaller. The dotted lines 1001 and 1004 in FIG. 28(A) and FIG. 28(B) indicate the planes (z-x planes) where the loop surfaces of the sub-coils 3-1 and 4-1 existed respectively.

FIG. 28(C) and FIG. 28(D) show the G-factor as a result of the simulation respectively on the cross sections 1001 and 1004, in the case where the AP direction was selected as the phase encoding direction. These figures represented values of each pixel two-dimensionally, obtained from the sensitivity distribution of each sub-coil, which were calculated according to the formula disclosed by the non patent document 2. In a similar manner, FIG. 28(E) and FIG. 28(F) show the G-factor as a result of the simulation respectively on the planes 1001 and 1004, in the case where the RL direction was selected as the phase encoding direction. As is known from the result being illustrated, it was found that in the receiver coil of the comparative example 1, the G-factor was unfavorable in some parts within the cross section where the sub-coils 3-1 and 4-1 existed (i.e., the area where the subject exist). This is because the large FOV receiver coils (sub-coils 3-1 and 4-1 in this example) such as solenoid coils had a higher sensitivity, relative to the sensitivity of the small FOV receiver coils (sub-coils 6-2 and 6-3 in this example), at least one pair of which was arranged in the phase encoding direction, and the sensitivity distribution of the large FOV receiver coil showed a homogeneous distribution.

A method for solving this problem is to enlarge the diameters of sub-coils 3-1 and 4-1, in order to achieve the sensitivity equivalent to or less than the sensitivity of the small FOV receiver coil, so that the sensitivity of the large FOV receiver coils (sub-coils 3-1 and 4-1 in this example) does not become too high relative to the sensitivity of at least one pair of small FOV receiver coils (sub-coils 6-2 and 6-3 in this example), which are arranged in the phase encoding direction (z-direction in this example). However, with this configuration, the sensitivity inside the subject may be deteriorated. In addition, for the subject having an elliptic cylinder shape, such as a human body, in order to prevent deterioration in sensitivity, it is considered that loops of large FOV sub-coils 3-1 and 4-1 may be formed along the surface of the subject, and appropriate multiple small FOV surface sub-coils may be arranged along each of the major axis (x-direction in the current case) and the minor axis (z-direction in the current case) of the imaging plane (elliptical section). However, a sensitivity profile of the large FOV sub-coil shows more homogeneity and a higher value in the minor axis direction than in the major axis direction. Therefore, if a high-speed imaging is performed by selecting the minor axis direction as the phase encoding direction, there is a tendency that the G-factor is more deteriorated than selecting the major axis as the phase encoding direction. As discussed, just employing the conventional large FOV receiver coil and small FOV receiver coil caused a problem that if it was tried to maintain a high sensitivity in the deep portion of the subject, there existed an imaging plane (a cross section where the large FOV exists) which was not available for imaging at high speed in an optional direction. On the other hand, it was found that this problem was solved by the arrangement of sub-coils provided by the present invention.

Comparative Example 2

As the comparative example 2, a simulation of the G-factor was performed, by employing the receiver coils with an arrangement of the sub-coil 5-1, the arrangement being different from the preferred embodiment described above. In the comparative example 2, the two conductive wires crossing each other, held by the sub-coil 5-1, were made to be parallel with the plane including the body axis of the subject (y-axis in this example). FIG. 29 illustrates an arrangement plan of the coils and the G-factor as a result. FIG. 29(A) is an arrangement plan of the sub-coils on the y-z plane viewed from the x-axis direction, and FIG. 29(B) is an arrangement plan of the sub-coils on the x-y plane viewed from the z-axis direction. The sub-coils 3-1 and 4-1 were identical to the sub-coils with the same numbers in the receiver coil as shown in FIG. 4.

The sub-coils 6-1-1 and 6-1-2 were obtained by optimally transforming the conventional large FOV coil 6-1 (a saddle coil, in this example), and arranged with appropriate overlaps. The sub-coils 7-1-1 and 7-1-2 were obtained by optimally transforming the sub-coil 7-1 providing the sensitivity distribution in the RL direction, and arranged with appropriate overlaps. These were the same as the sub-coils indicated by the same numerals, which were used in the aforementioned preferred embodiments. The sub-coils 5-8-1 and 5-8-2 were obtained by changing the direction of the two conductive wires crossing each other, held by the two sub-coils 5-1-1 and 5-1-2 explained with reference to FIG. 27(A) and FIG. 27(B), from the state being crossing the plane including the body axis (y-axis) of the subject to the state being substantially parallel with the plane including the body axis (y-axis) of the subject.

The sub-coils 5-8-1 and 5-8-2 overlapped one another appropriately, thereby rendering the electromagnetic coupling sufficiently small. However, this arrangement was different from FIG. 12, and two cross points 5-4 and 5-5 held by the sub-coil 5-1 did not exist on the same plane as the cross section (1001) where the sub-coil 3-1 existed. In FIG. 29(A) and FIG. 29(B), the reference numeral 1001 and 1004 indicate the planes (z-x planes) where the loop surfaces of the sub-coils 3-1 and 4-1 existed respectively.

FIG. 29(C) and FIG. 29(D) show the G-factor as a result of the simulation respectively on the cross sections 1001 and 1004, in the case where the AP direction (z-direction in this example) was selected as the phase encoding direction. These figures represented values of each pixel two-dimensionally, obtained from the sensitivity distribution of each sub-coil, which were calculated according to the formula disclosed by the non patent document 2. According to the result being illustrated, it was found that when the sub-coils were arranged so that the directions of the two conductive wires crossing each other, held by the sub-coil 5-1, were made to be almost parallel with the plane including the body axis (y-axis in this example) of the subject, this deteriorated the G-factor.

In a similar manner, on the basis of the arrangement plan of the sub-coils as shown in FIG. 27, the G-factors in various arrangement patterns were obtained, while changing the arrangement manner of each of the sub-coils. Consequently, if the sub-coils were arranged in such a manner that the two cross points 5-4 and 5-5 indicated in FIG. 12 were placed on the plane approximately identical to the plane 1001 where the current loop of the large FOV coil 3-1 existed, the result was that the G-factor was improved most. Accordingly, with the configuration above, an image having the highest S/N can be expected.

<Second Embodiment>

Next, with reference to FIG. 30, an explanation will be made regarding an external configuration of the receiver coil unit according to the second embodiment. FIG. 30 illustrates the second embodiment, and FIG. 30(A) is a perspective view when a test object is set, FIG. 30(B) is a cross sectional view on a plane perpendicular to the body axis, FIG. 30(C) is a perspective view in the state where an outer support is open, and FIG. 30(D) is an external view when an inner support is open.

As illustrated, also in the present embodiment, a support for supporting a coil conductor has a dual structure made up of the outer support 20-2 and the inner support 20-1. As shown in FIG. 30(C), the outer support 20-2 has a structure that is dividable into the back side and chest side of the subject, and it is openable at one side of the test object 103. As shown in FIG. 30(D), the inner support 20-1 is openable from the upper side of the test object 103 (the ventral side of human being placed on his or her back) toward the both sides. Such configuration as described above may facilitate installing of the coil on the test object.

The inner support 20-1 is made of a flexible sheet-like material, and it supports the sub-coils 6-1 and 7-1, for instance. Since the sub-coils 6-1 and 7-1 do not include a coil pattern (conductor) above the subject, it is possible to allow the sub-coils 6-1 and 7-1 to open toward both sides at the part where the coil pattern does not exist. On both ends of the outer support 20-1, designed to be closed, it is preferable to provide fixtures 20-5 respectively, which allow a stable mounting of the support on the subject. The use of the flexible sheet-like material may ease an oppressive feeling to the subject 103.

The outer support 20-2 supports sub-coils 3-1, 4-1, and 5-1, for instance. A part at which the outer support 20-2 is separated is provided with connectors 20-4, and fixtures 20-3-1 and 20-3-2. With this configuration, it is easy to separate and attach the upper and lower parts of the support 20-2. It is to be noted that the figure illustrates the state where the support 20-2 is entirely opened, but the support may be openable block by block.

In the total-body use receiver coil according to the present embodiment, the inner support 20-1 is made of a flexible material, and the outer support 20-2 is placed at a certain distance from the subject. Accordingly, even though it is structured in such a manner that the subject is covered entirely, one can fully enjoy the advantage of the vertical magnetic field MRI apparatus that the oppressive feeling can be reduced. Furthermore, the inner support 20-1 is made of a flexible material, thereby allowing the inner support to tightly adhere to the subject in any different size. As for the outer support 20-2, the part of lower side (back side) is commonly used, and multiple types of different sizes may be prepared for the part of upper side (chest side, ventral side), thereby enabling adaptation to the subject in any different size (other embodiment).

As described above, the magnetic resonance imaging apparatus according to the present embodiment includes the static magnetic field generation means for generating a static magnetic field vertically, an imaging means for applying an RF magnetic field and a gradient magnetic field on a test object placed in the static magnetic field, and a receiving means for receiving a nuclear magnetic resonance signal generated from the test object, the receiving means being provided with a receiver coil unit made up of multiple types of sub-coils, wherein, the receiver coil unit comprises a bed coil unit whose longitudinal direction agrees with a body axis direction of the test object and an upper coil unit which is detachably mounted on the bed coil unit; the bed coil unit is provided with a carrying surface for placing the test object and multiple lower sub-coils arranged in a lower part of the carrying surface; the upper coil unit is provided with multiple upper sub-coils which are connected to the lower sub-coils; the upper sub-coils are arranged being separated into an inner support being flexible to cover the carrying surface and an outer support being flexible to cover an external side of the inner support; and the upper sub-coils and the lower sub-coils are connected by mounting the upper coil unit on the bed coil unit to form the multiple types of sub-coils.

In the case above, it is possible to configure such that the bed coil unit is provided with multiple joint support parts formed on both sides of the carrying surface along the longitudinal direction, and the upper coil unit incorporates a pair of joining sections having multiple joint parts connectable with the multiple joint support parts, the outer support whose both ends are supported by the pair of the joining sections, and a pair of inner supports having one end mounted on the joining section and the other end being free end, and the joint support parts and the joint parts are connected to form the multiple sub-coils.

Further in the case above, it is possible to configure such that the lower sub-coils arranged in the bed coil unit are divided into multiple blocks each having the same arrangement along the longitudinal direction, and the upper coil unit is connected with one of the multiple blocks, thereby forming independent multiple sub-coils, which cover the external side of the test object placed on the carrying surface.

Further in the case above, it is possible to configure such that the inner support is provided with an extending part which extends one end in the longitudinal direction, farther than the outer support, and when the multiple upper coil units are mounted on the bed coil unit along the longitudinal direction, the extending part overlaps the other end side of the inner support of other upper coil unit.

Further in this case, the outer support is provided with a sub-coil which has a coil conductor pattern existing above the test object, and the inner support is provided with a sub-coil which has no coil conductor pattern existing above the test object. In addition, it is further possible to install the joint support parts rotatably to be opened toward both ends respectively, in the longitudinal direction, or the multiple joint support parts formed along the longitudinal direction are provided in multiple rows on the both sides of the carrying surface.

A magnetic resonance imaging apparatus according to another embodiment, includes a static magnetic field generation means for generating a static magnetic field vertically, an imaging means for applying an RF magnetic field and a gradient magnetic field to a test object placed in the static magnetic field, and a receiving means for receiving a nuclear magnetic resonance signal generated from the test object, the receiving means being provided with a receiver coil unit made up of multiple types of sub-coils, wherein, the receiver coil unit comprises a bed coil unit whose longitudinal direction agrees with a body axis direction of the test object, and multiple upper coil units detachably mounted on the bed coil unit along the longitudinal direction of the bed coil unit; the bed coil unit is provide with a carrying surface for placing the test object in the center of lateral direction which is orthogonal to the longitudinal direction, multiple joint support parts arranged along the longitudinal direction on the both sides of the lateral direction of the carrying surface, and multiple subsets of sub-coils connected with the joint support parts on both sides and arranged in the lateral direction; the upper coil unit incorporates a pair of joining sections arranged on both sides of the lateral direction, an outer support whose ends are supported by the pair of the joining sections, and a pair of inner supports having one end mounted on the joining section and the other end being free end; the joining section has a stick-like appearance and comprises along the longitudinal direction multiple joint parts to be connected with the joint support parts are provided therein; the inner support and the outer support have a flexible thin plate-like appearance, the subsets of sub-coils being arranged therein; and in each of the outer support and the inner support, multiple openings are formed in accordance with the arrangement of the sub-coils; and the upper coil unit is allowed to be coupled with the bed coil unit via a linkage of the joint support parts and the joint parts to form multiple sub-coils which cover an external side of the test object placed on the carrying surface.

In this case, it is possible that the subsets of sub-coils arranged on the bed coil unit are divided into multiple blocks, each having an arrangement of the same subset of sub-coils along the longitudinal direction, the upper coil unit is connected with one of the multiple blocks, and independent multiple sub-coils are formed to cover the external side of the test object placed on the carrying surface.

It is further possible that the outer support is provided with a sub-coil which has a coil conductor pattern existing above the test object, and the inner support is provided with a sub-coil which has no coil conductor pattern existing above the test object.

Furthermore, it is possible to configure such that the inner support is provided with an extending part which extends one end in the longitudinal direction, farther than the outer support, and when the multiple upper coil units are mounted on the bed coil unit along the longitudinal direction, the extending part overlaps the other end side of the inner support of other upper coil unit.

Furthermore, it is possible to install the joint support parts rotatably to be opened toward both ends in the lateral direction, or multiple rows of the joint support parts may be provided on the both sides in the lateral direction of the carrying surface.

INDUSTRIAL APPLICABILITY

According to the present invention, it is possible to provide a receiver coil made up of multiple sub-coils, with a favorable G factor. A combination of the sub-coils constituting the receiver coil can be connected continuously, without increasing the number of channels, in a direction orthogonal to the first coil current loop, for example, in the body axis direction of a subject, thereby constituting a total-body use receiver coil with a superior mountability. Since the G-factor is favorable, an image with a high S/N can be obtained. In particular, in a reduced-time imaging method which removes image aliasing by utilizing the sensitivity distribution of the sub-coils, it is possible to obtain a satisfactory image in any phase encoding direction.

BRIEF DESCRIPTION OF DRAWINGS

FIG. 7 illustrates the third type coil constituting the receiver coil shown in FIG. 4;

FIG. 10 illustrates the fifth type coil constituting the receiver coil shown in FIG. 4;

FIG. 12 illustrates arrangements of the first coil and the third coil;

FIG. 13 illustrates electromagnetic features between the first type coil and the third type coil, and between the second type coil and the third type coil;

FIG. 17 is a structural illustration of the bed coil unit;

FIG. 21 illustrates the receiver coil unit according to other embodiment;

FIG. 27 shows the G factor, when the receiver coil according to the first embodiment was employed;

FIG. 28 illustrates an example of the G factor when the receiver coil according to the comparative example 1 was employed;

FIG. 29 illustrates an example of the G factor when the receiver coil according to the comparative example 2 was employed.

Figure 1:
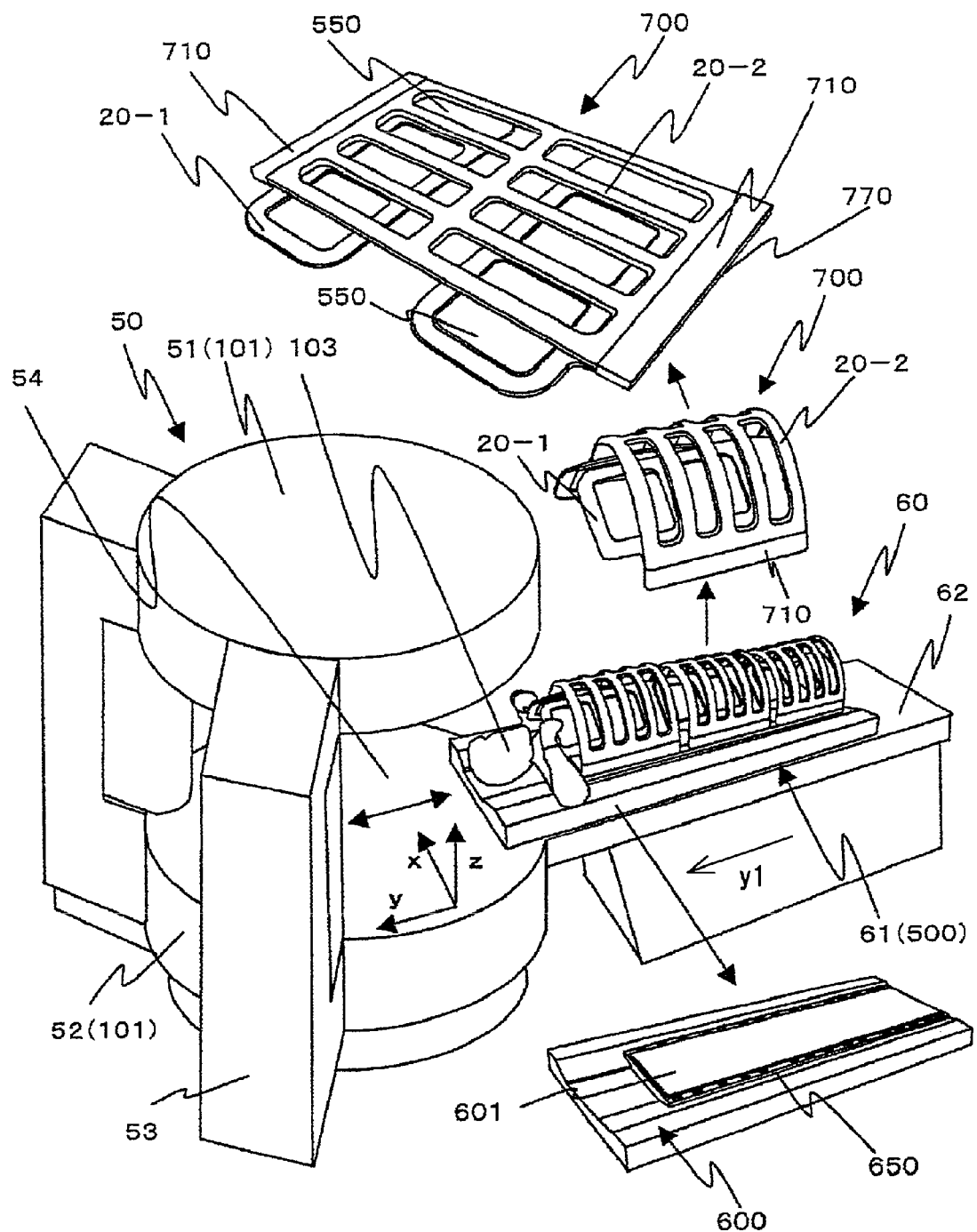
FIG. 1 illustrates a schematic structure of the MRI apparatus.
Figure 2:
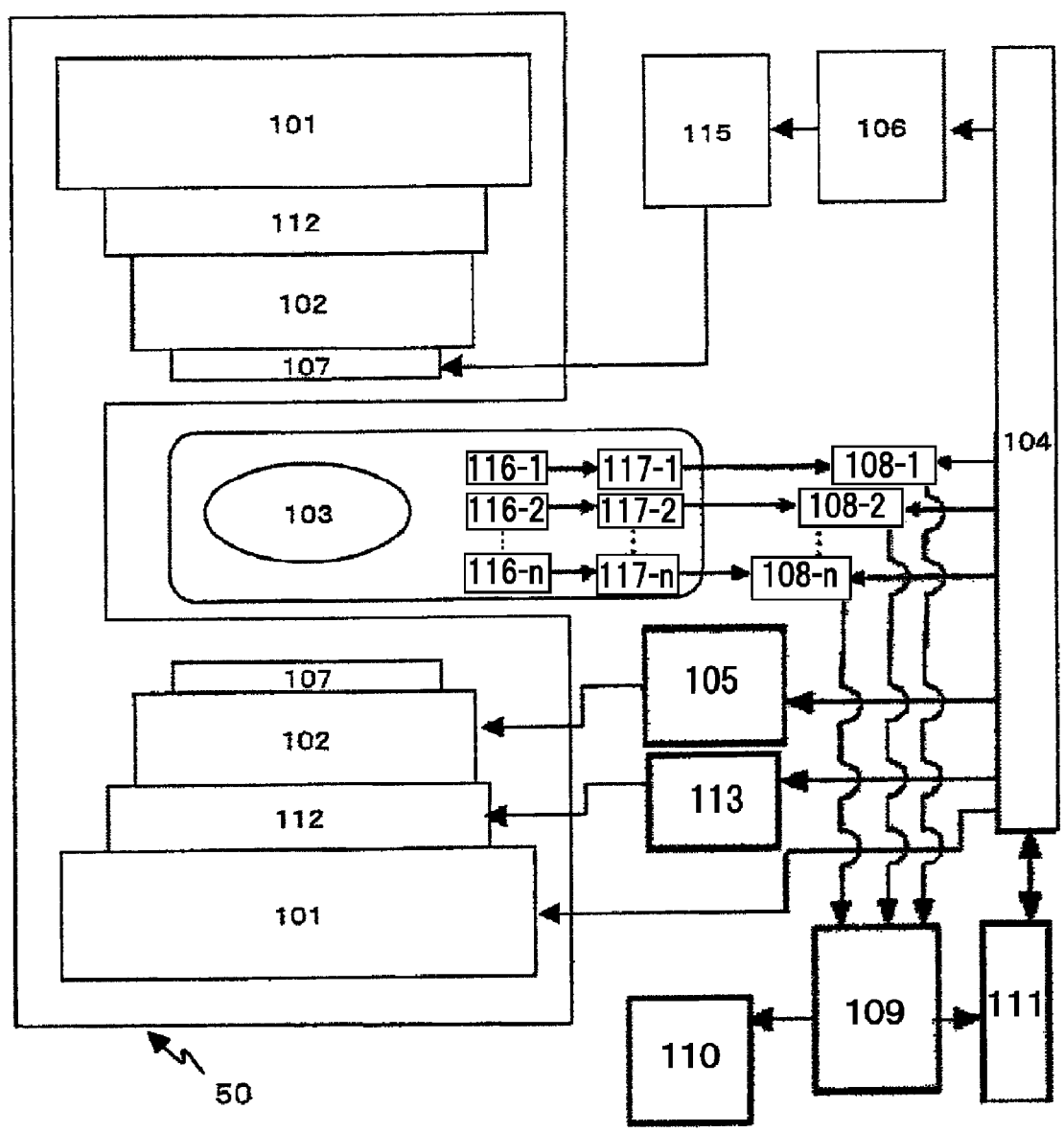
FIG. 2 schematically illustrates an apparatus block diagram of the MRI apparatus.
Figure 3:
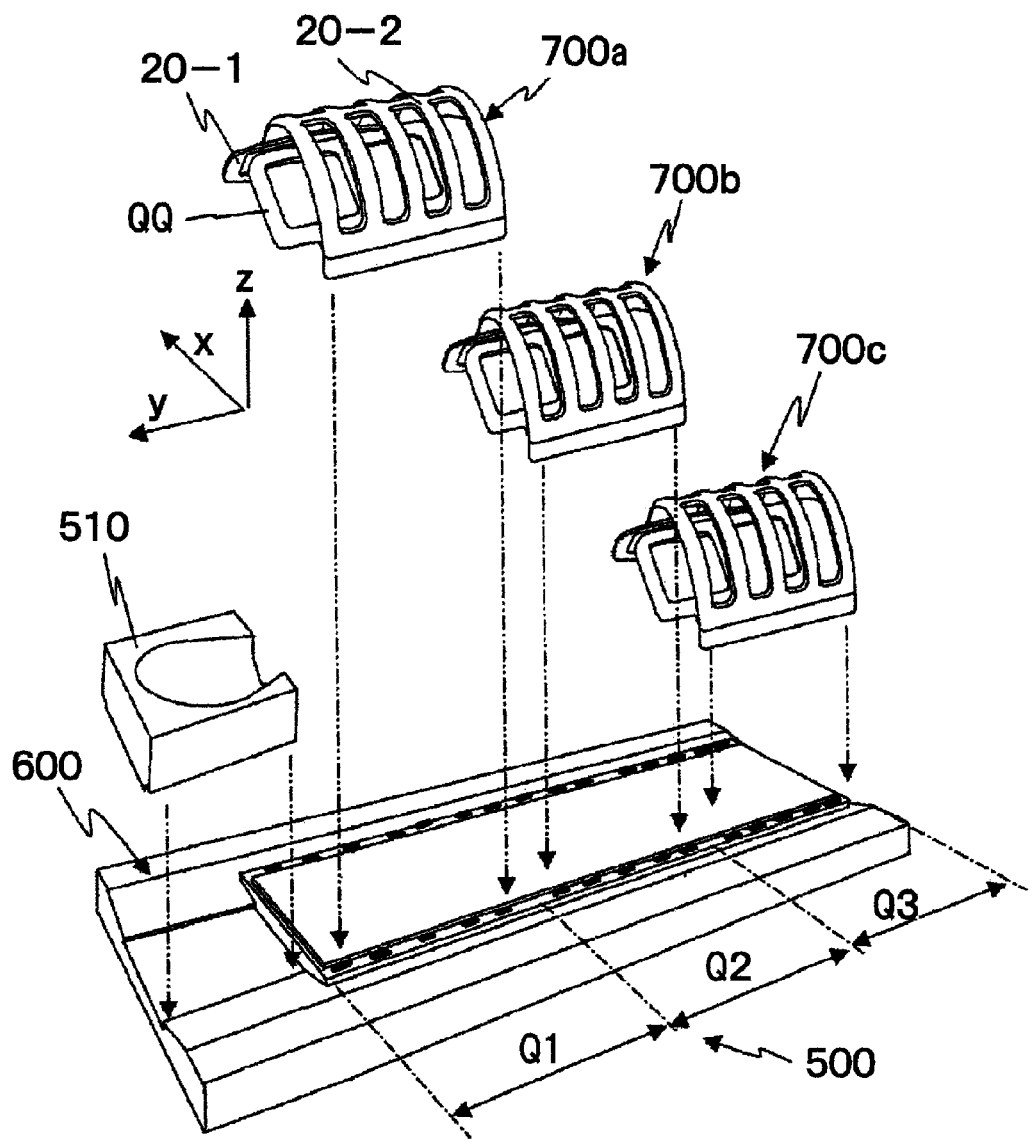
FIG. 3 illustrates a parts breakdown of the receiver coil unit according to the first embodiment.
Figure 4:
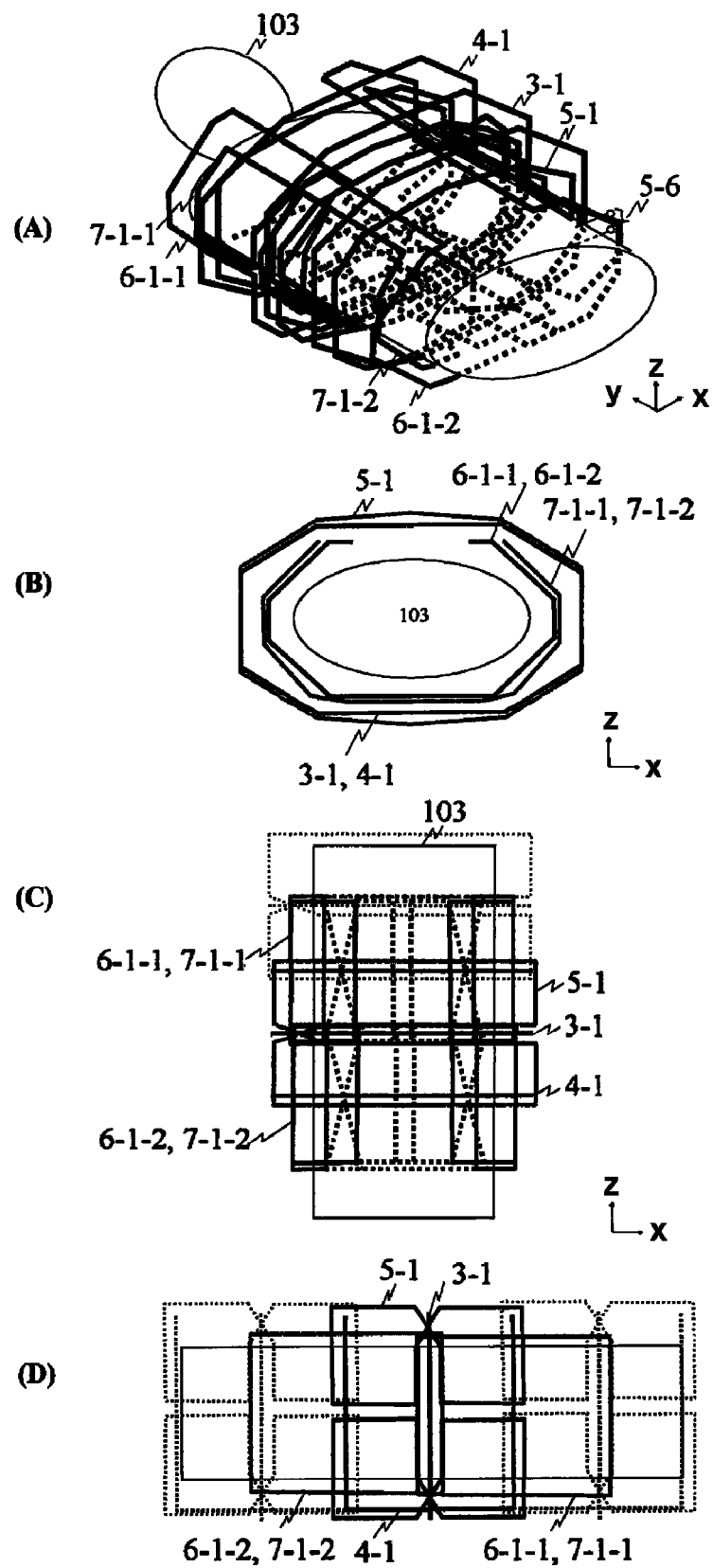
FIG. 4 illustrates a configuration of the receiver coil according to the first embodiment.
Figure 5:
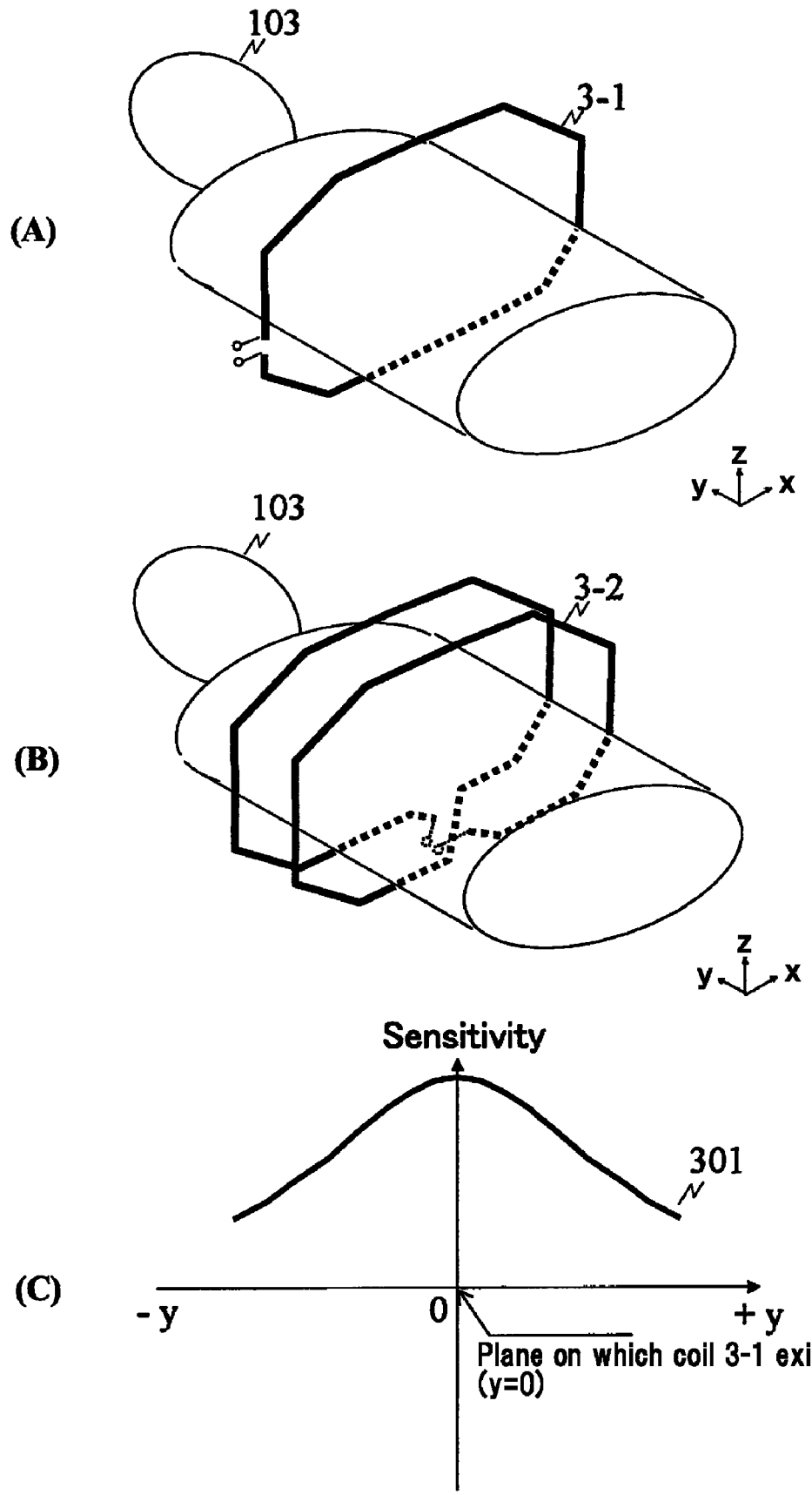
FIG. 5 illustrates the first type coil constituting the receiver coil shown in FIG. 4, and a characteristic of the first type coil.
Figure 6:
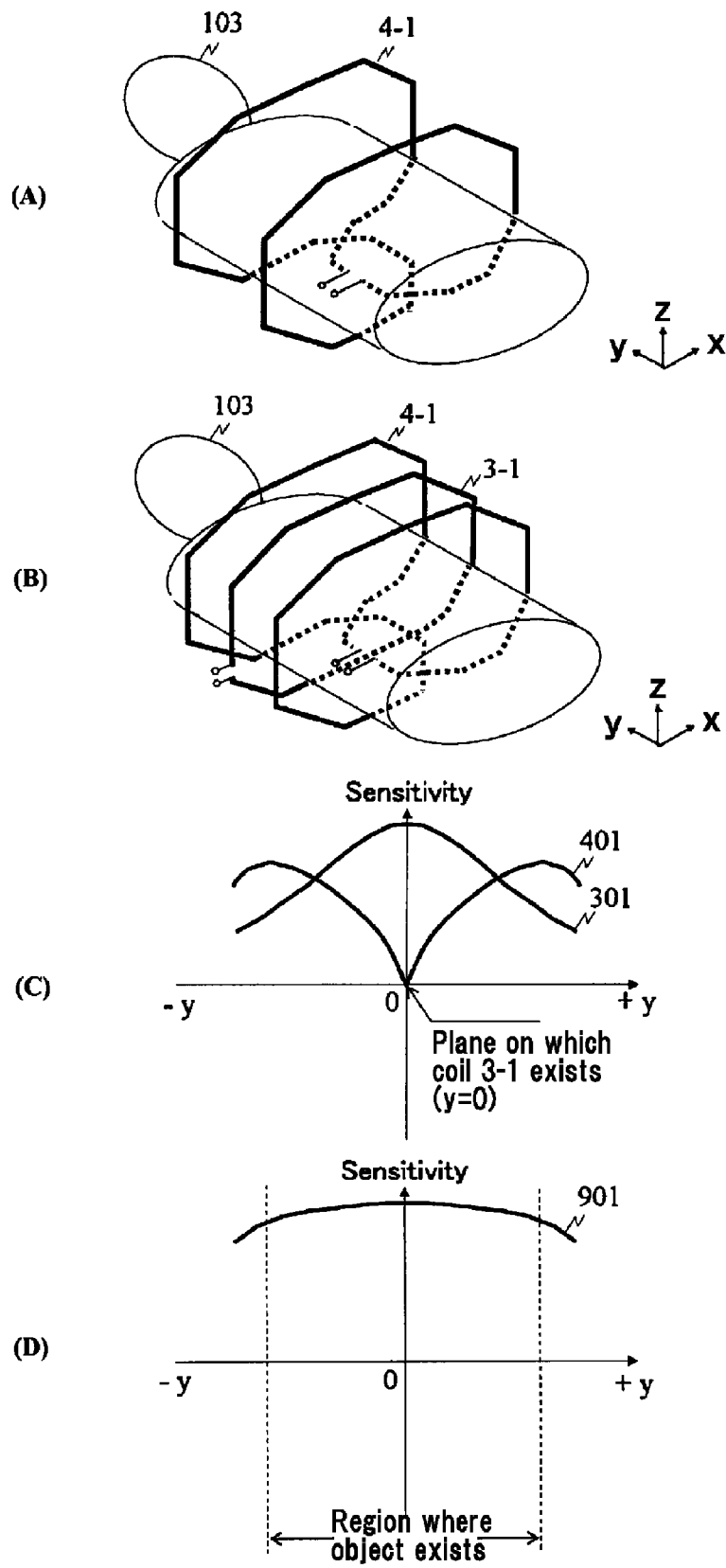
FIG. 6 illustrates the second type coil constituting the receiver coil shown in FIG. 4, and a characteristic of the second type coil.
Figure 8:
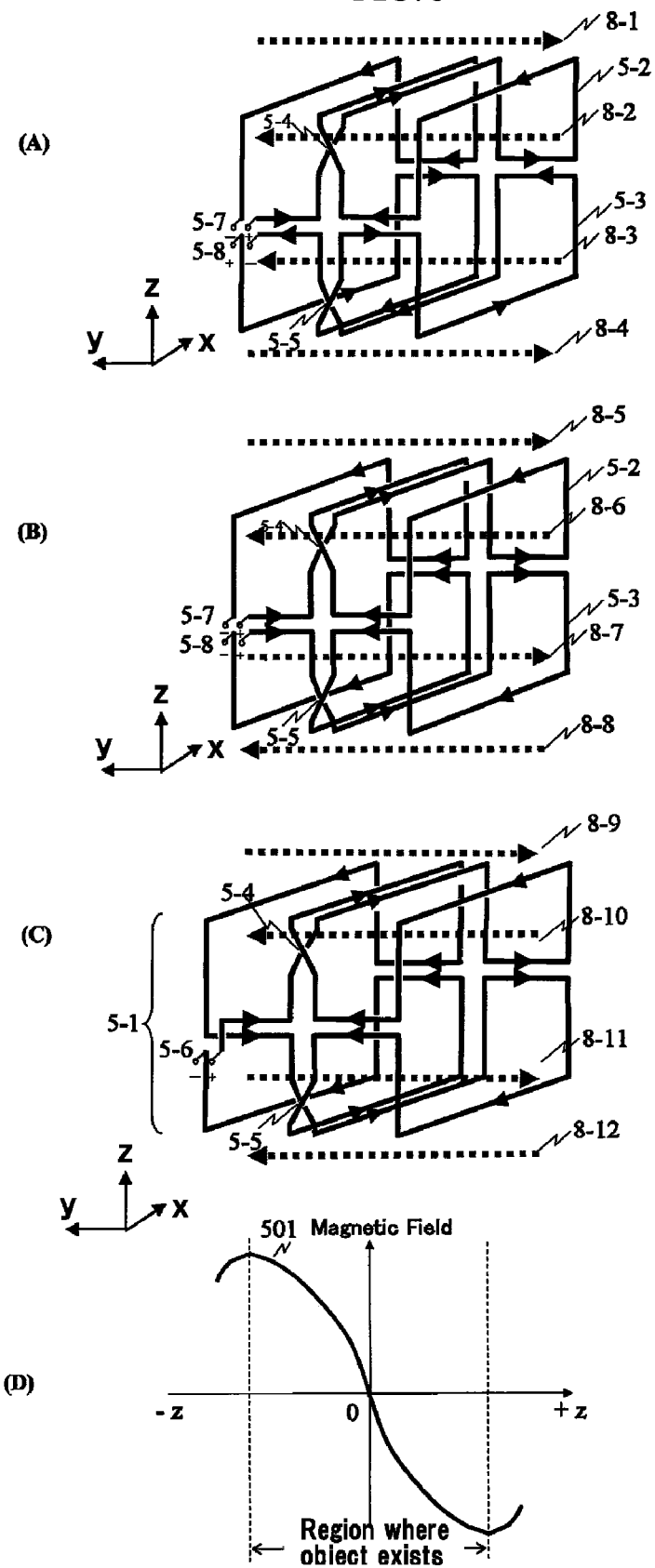
FIG. 8 illustrates a characteristic of the third type coil.
Figure 9:
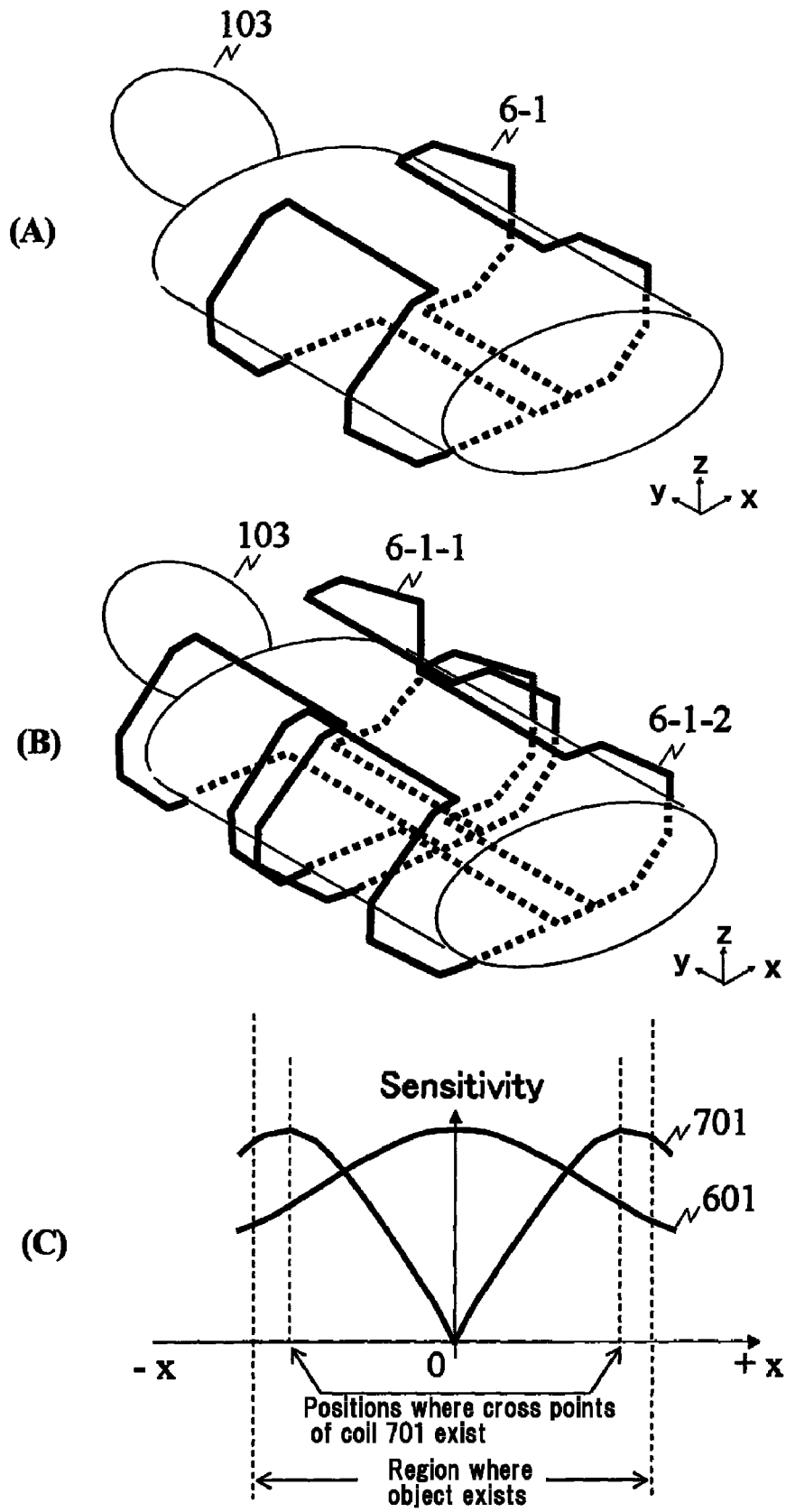
FIG. 9 illustrates the fourth type coil constituting the receiver coil shown in FIG. 4, and a characteristic of the fourth type coil.
Figure 11:
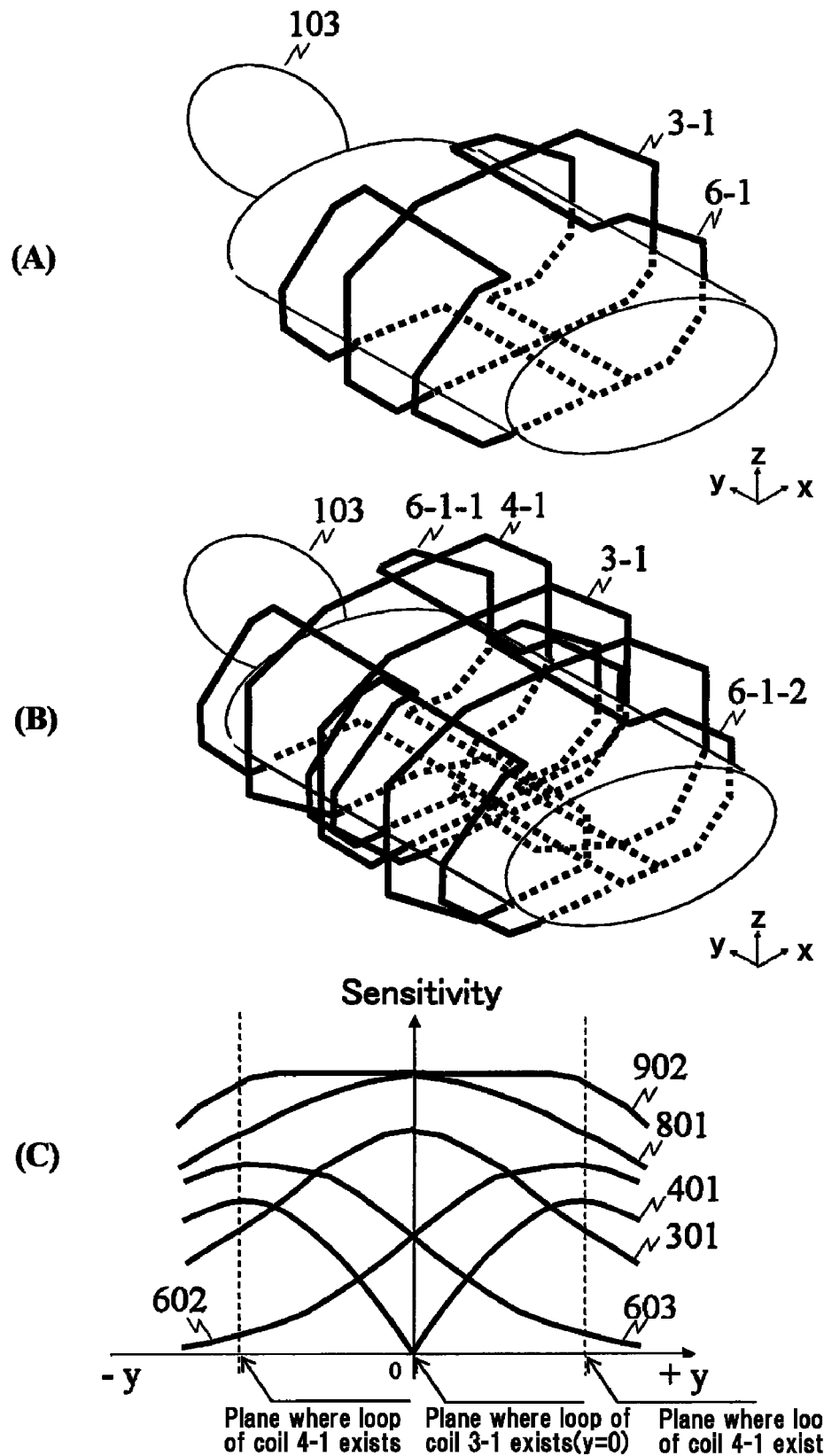
FIG. 11 illustrates arrangements of the first type coil, the second type coil, and the fourth type coil, and the characteristics thereof.
Figure 14:
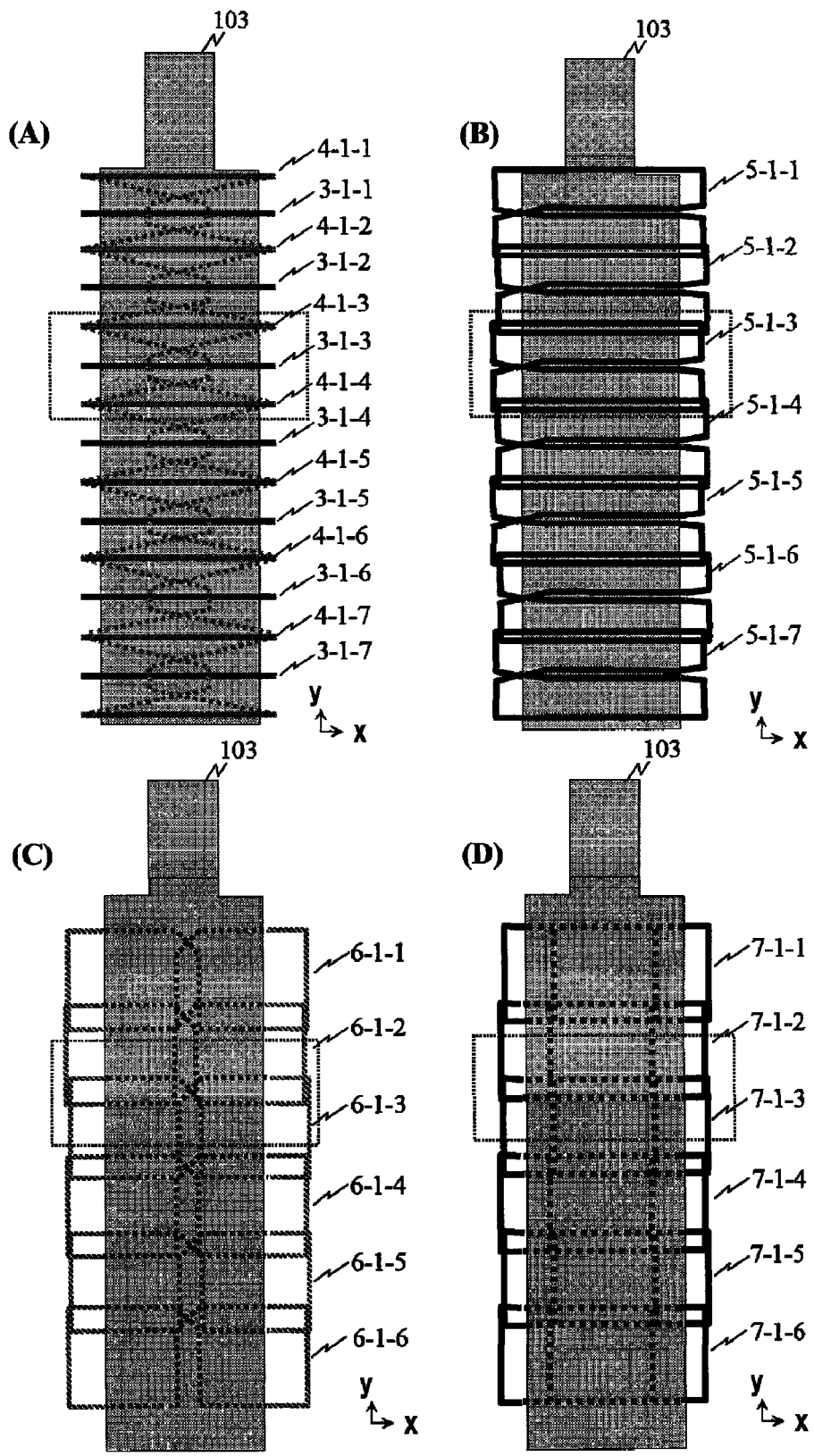
FIG. 14 illustrates an arrangement example in the case where the receiver coil according to the first embodiment is applied to a total-body-use receiver coil.
Figure 15:
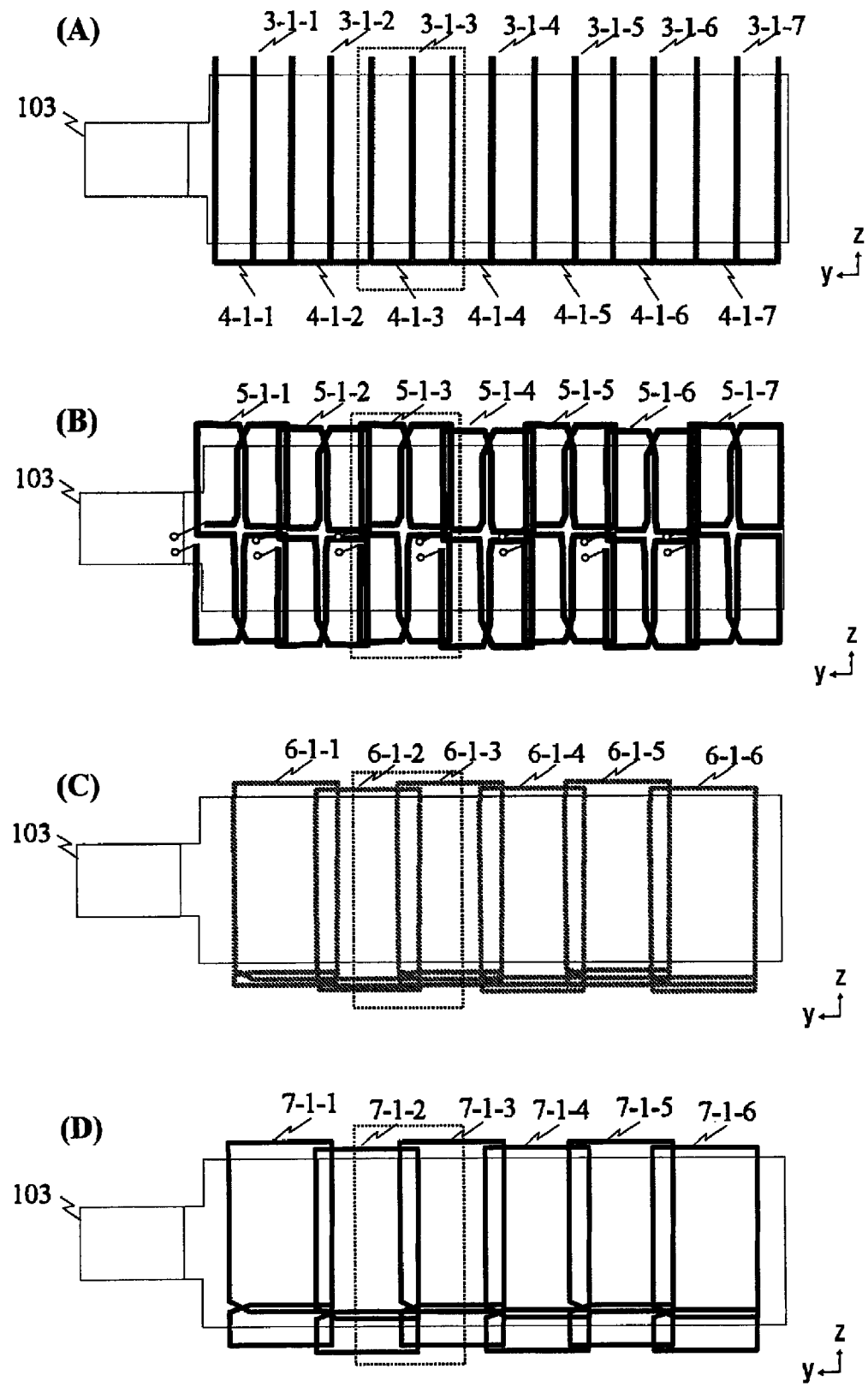
FIG. 15 illustrates an arrangement example in the case where the receiver coil according to the first embodiment is applied to a total-body-use receiver coil.
Figure 16:
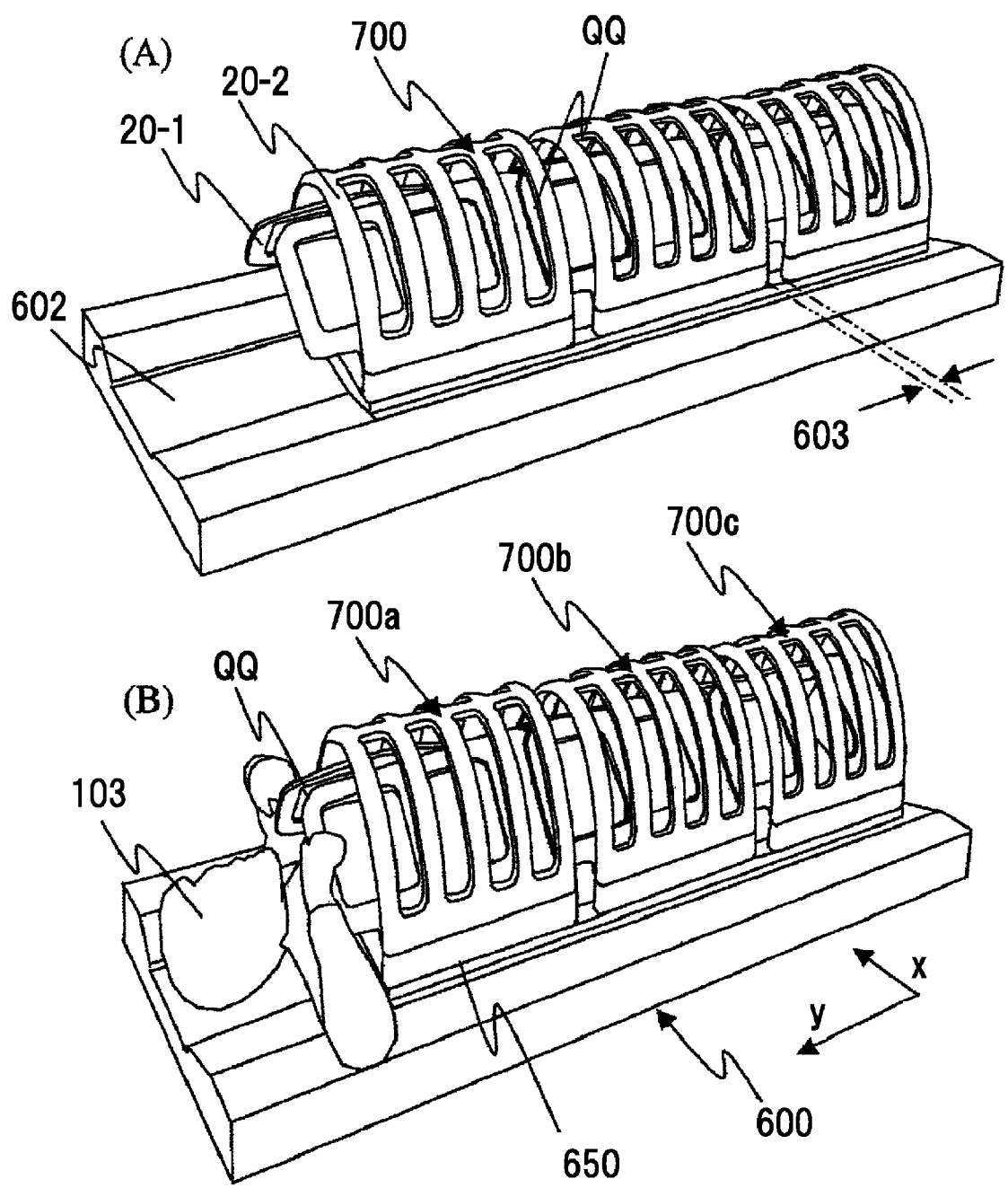
FIG. 16 is an external perspective view of the receiver coil unit.
Figure 18:
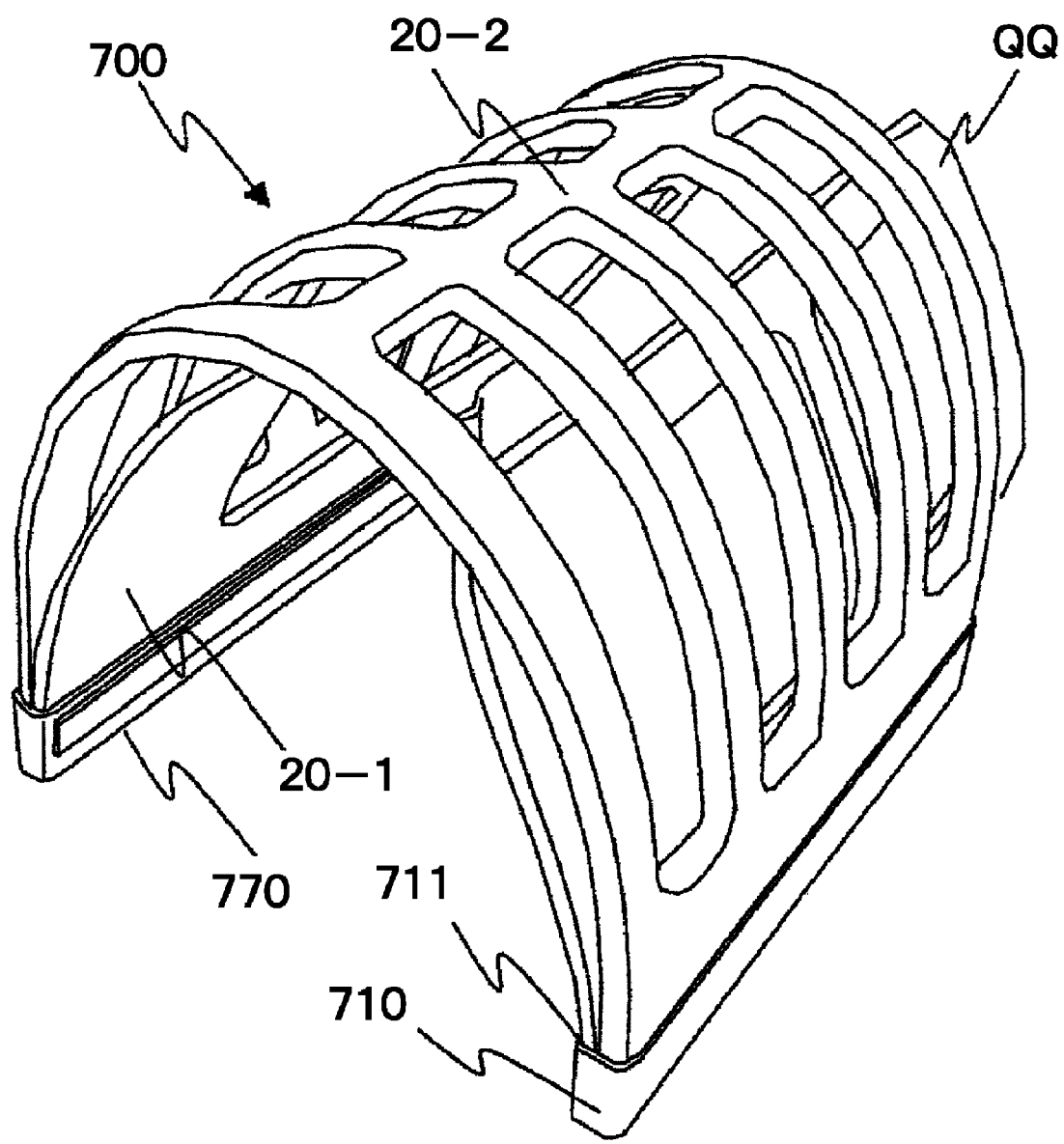
FIG. 18 is an external view in the state where the upper coil unit is set.
Figure 19:
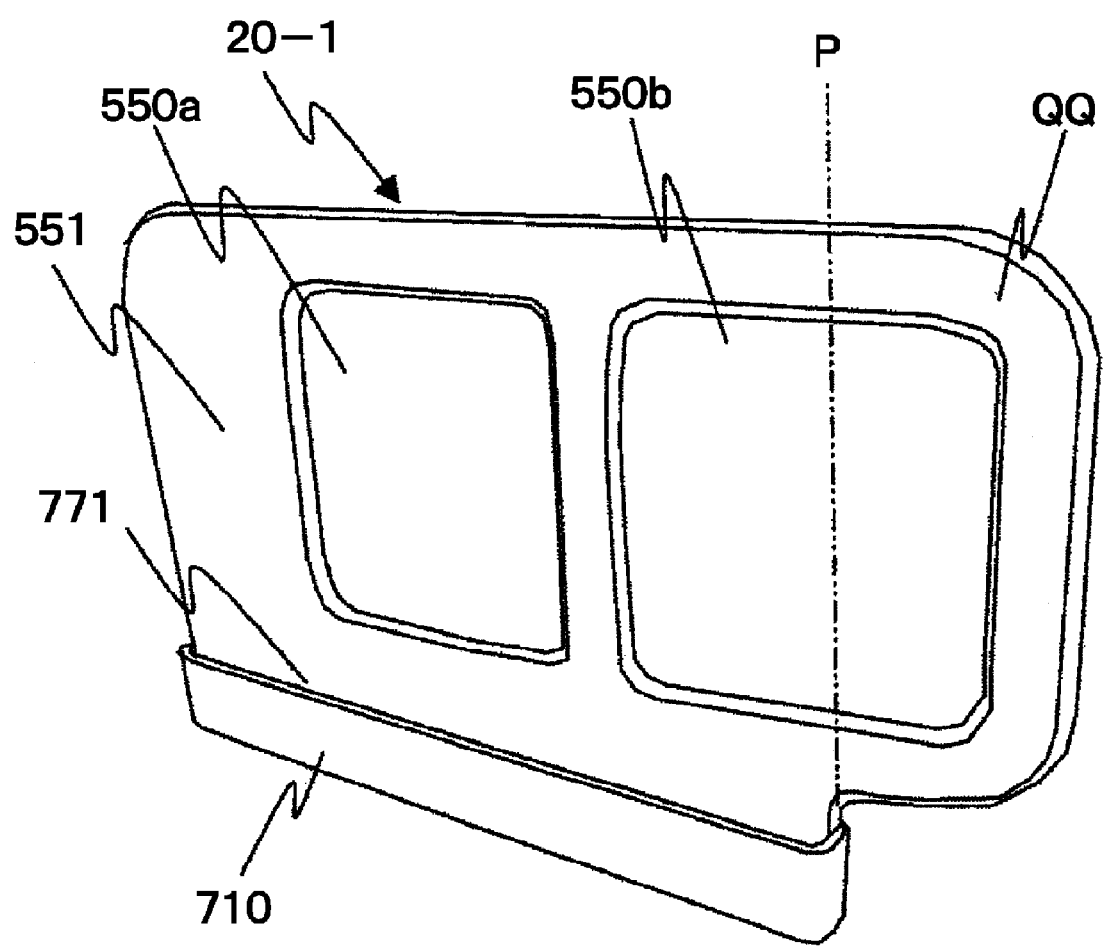
FIG. 19 is an external perspective view of the inner support.
Figure 20:
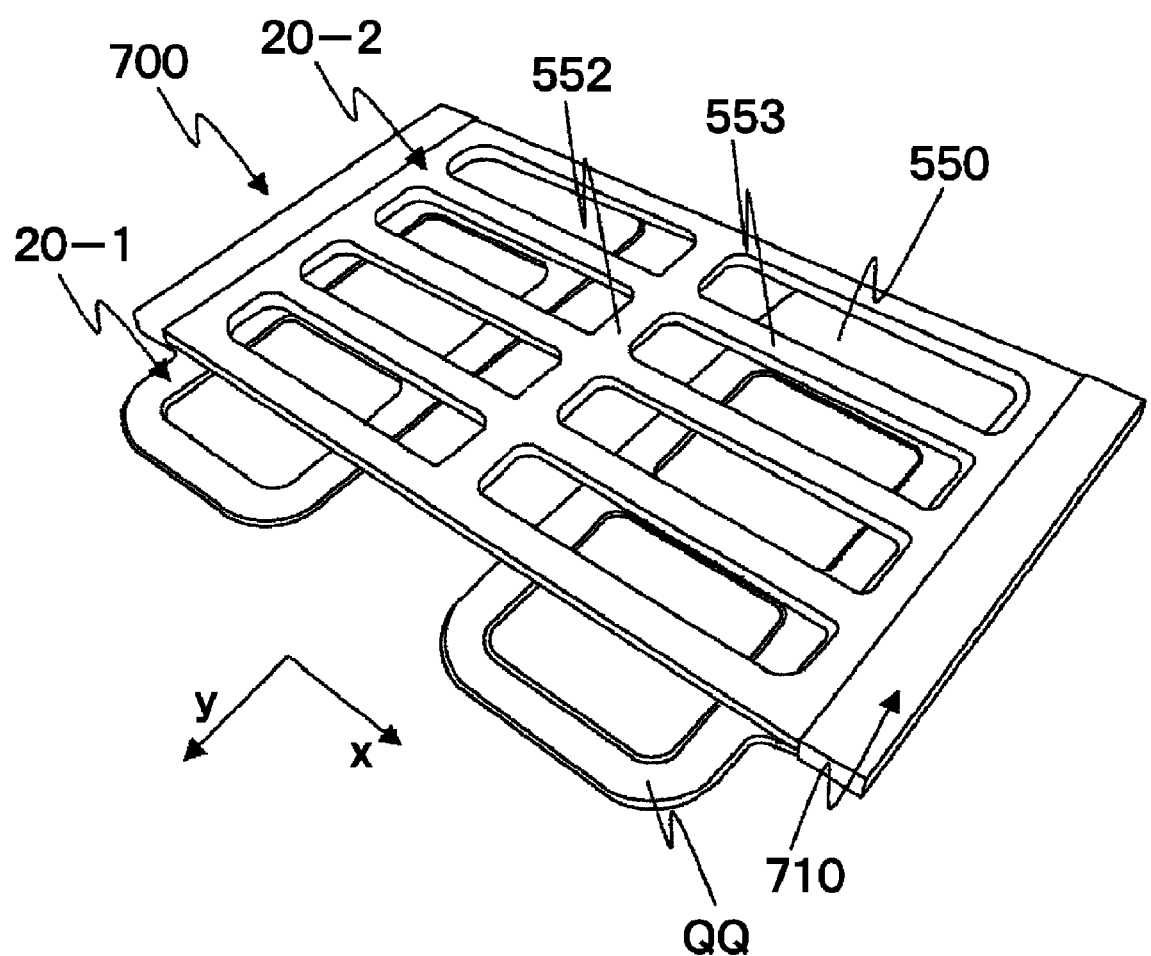
FIG. 20 is an external view in the state where the upper coil unit is made flat.
Figure 22:
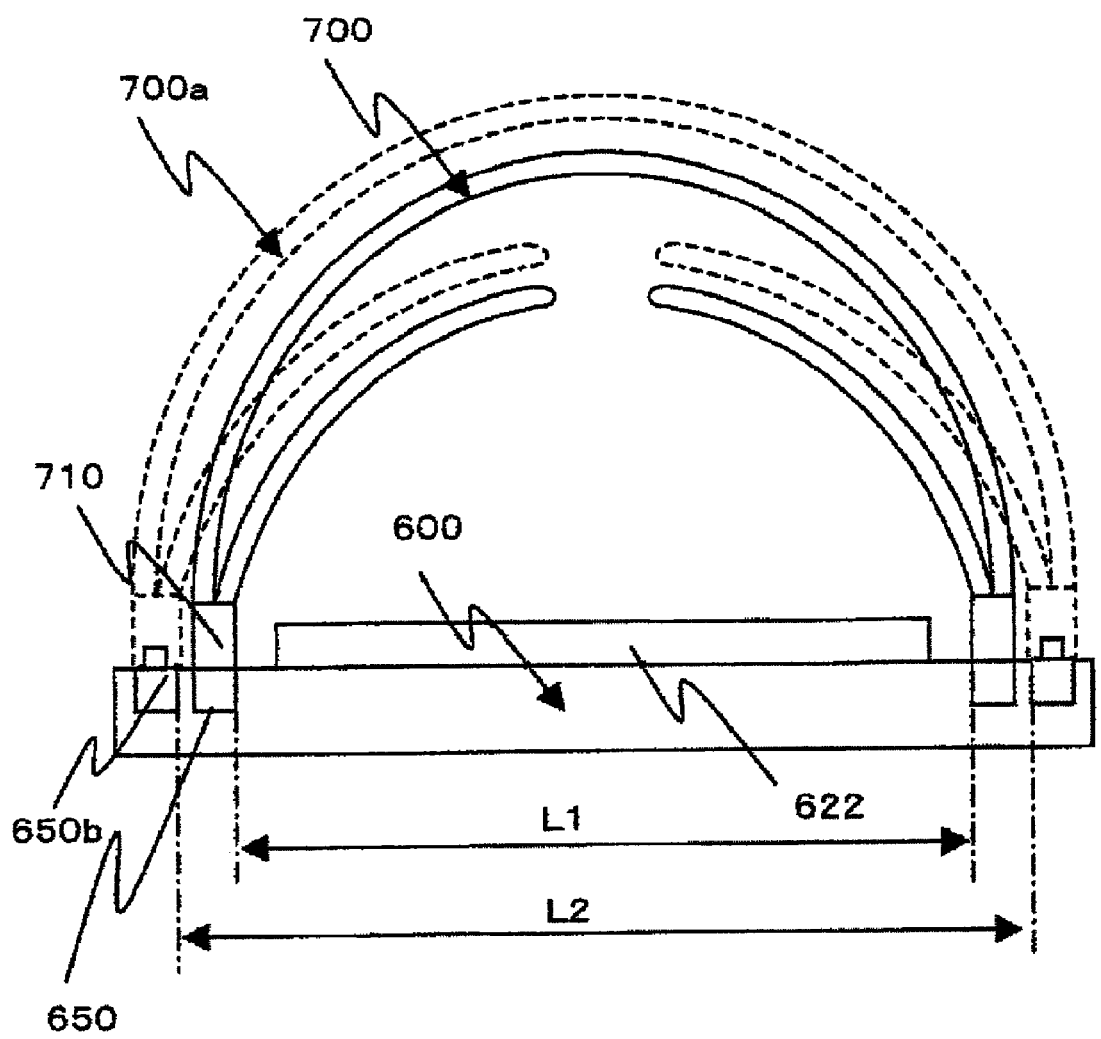
FIG. 22 illustrates the receiver coil unit according to other embodiment.
Figure 23:
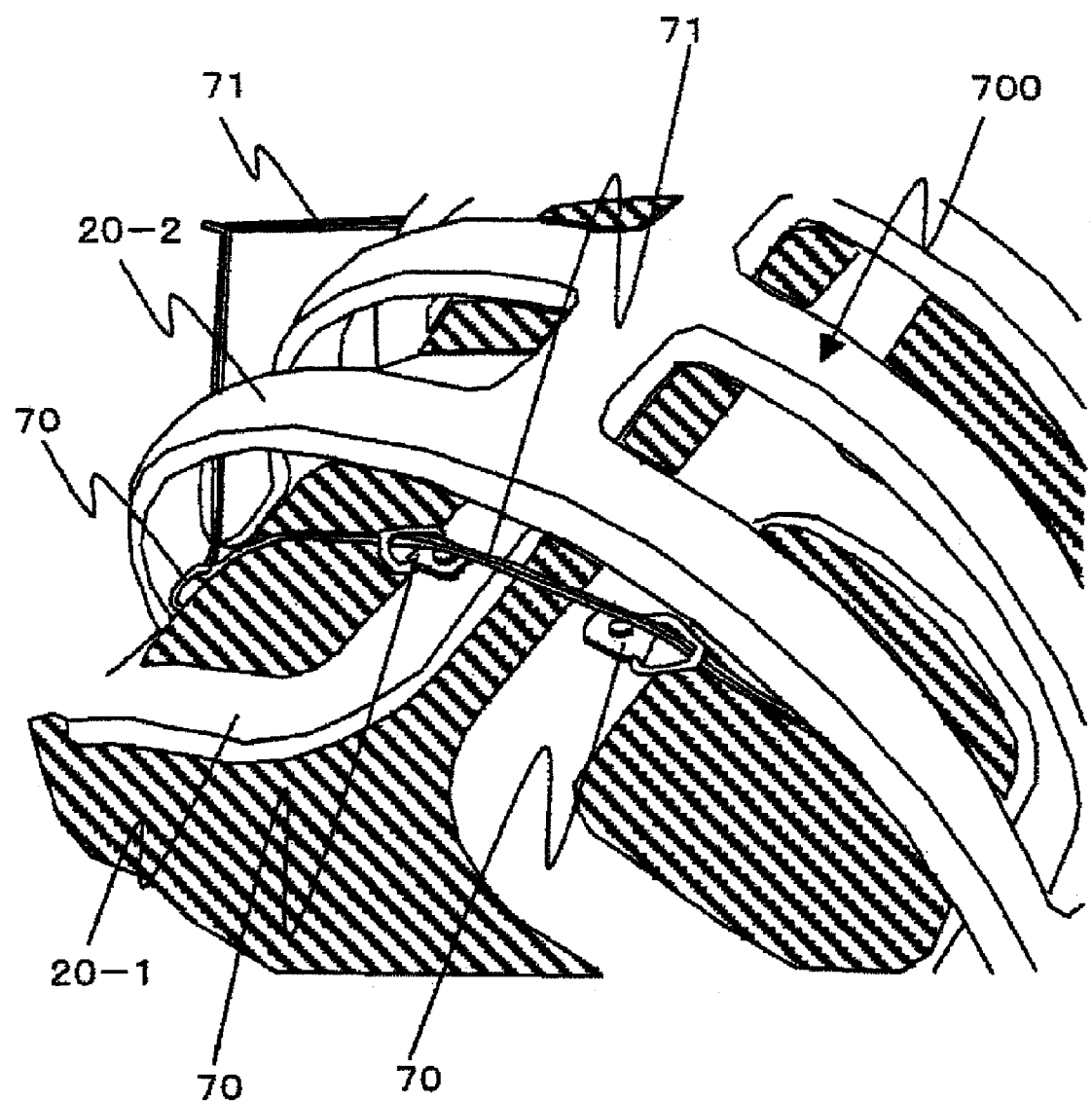
FIG. 23 is a partial perspective view showing a way how to install the free ends of the inner support.
Figure 24:
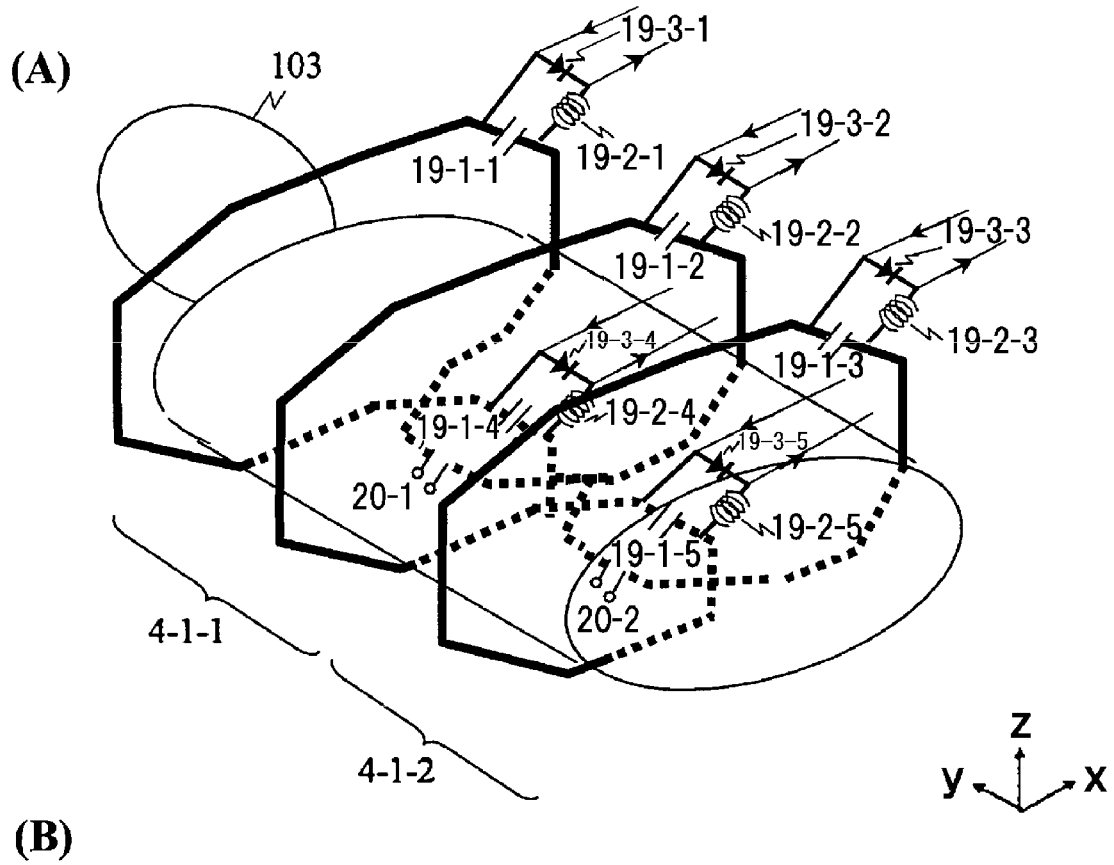
FIG. 24 shows a switching circuit of the first type coil and the second type coil.
Figure 25:
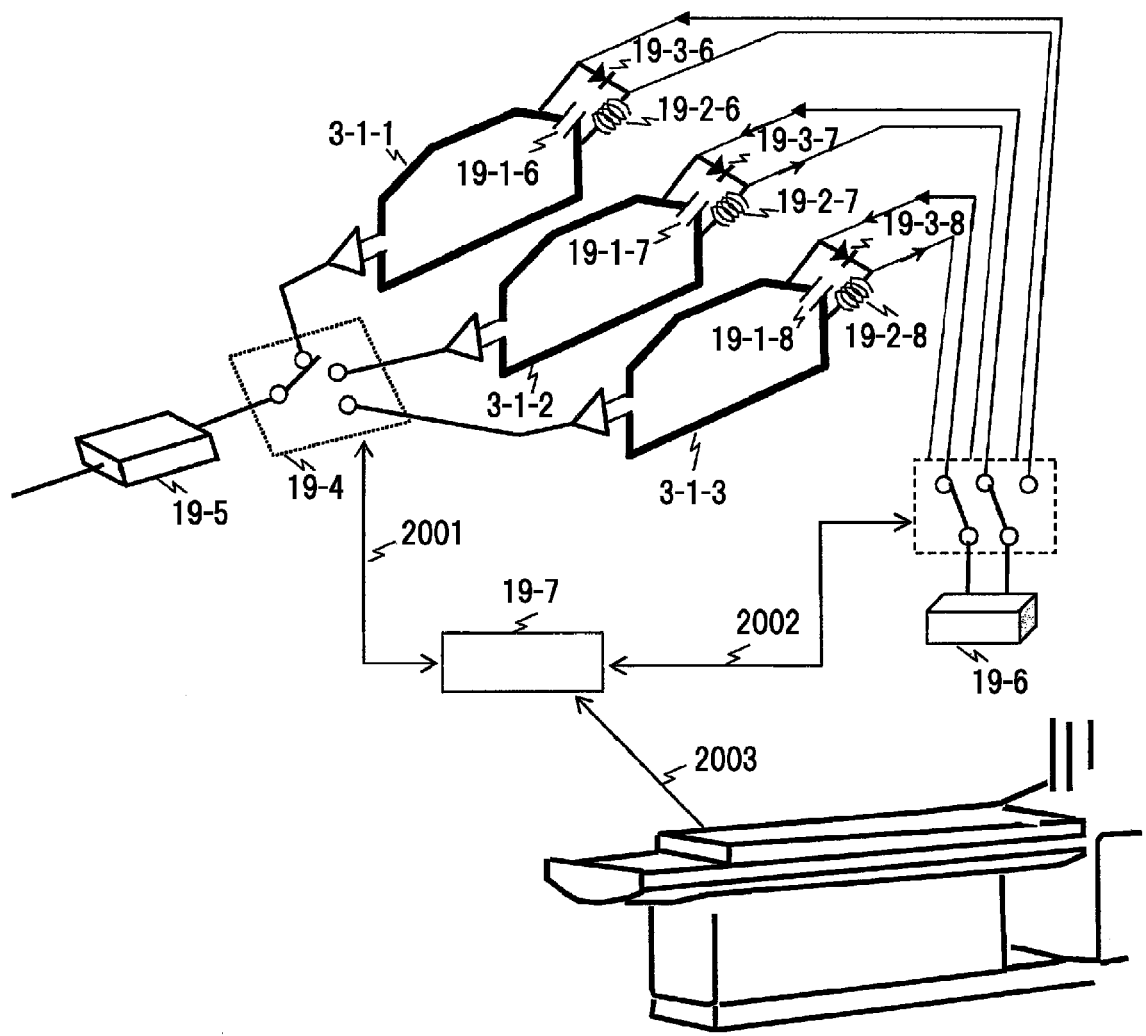
FIG. 25 shows a control system of the receiver coil according to the first embodiment.
Figure 26:
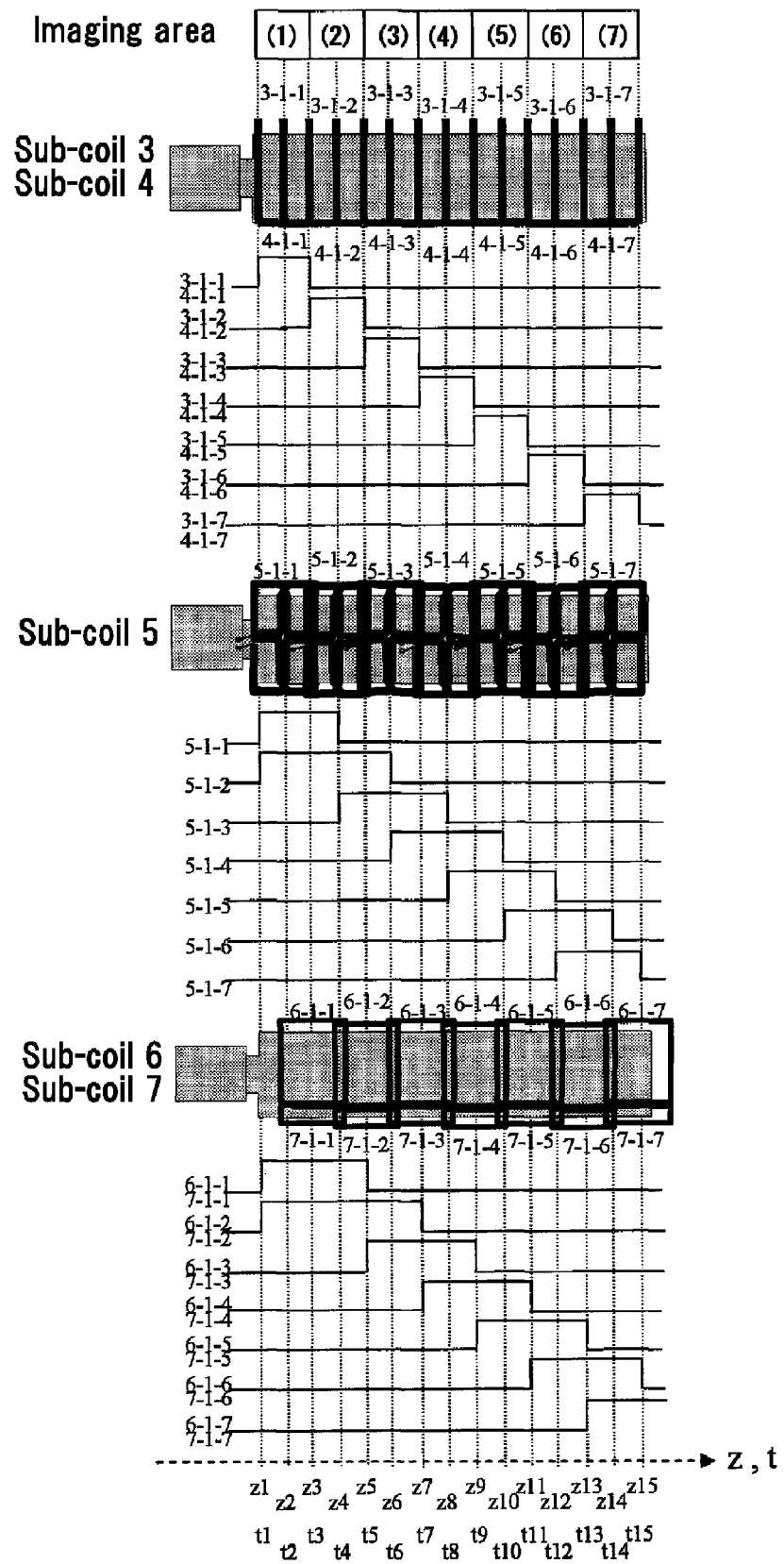
FIG. 26 shows a control sequence of the receiver coil according to the first embodiment.
Figure 30:
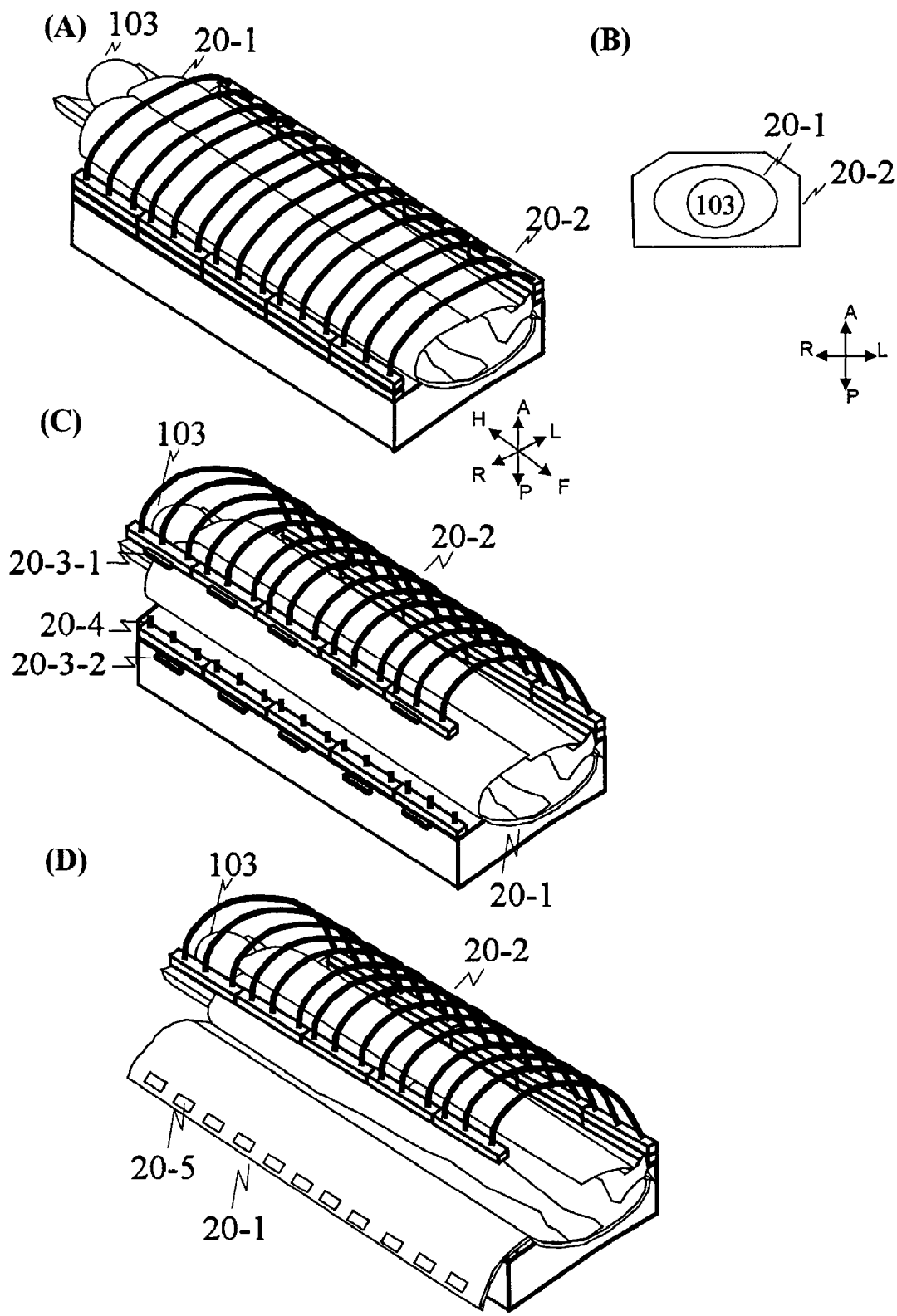
FIG. 30 is an external view showing the receiver coil according to the second embodiment

DENOTATION OF REFERENCE NUMERALS 3-1 (3-1-1 TO 3-1-7): FIRST SUB-COIL (FIRST TYPE SUB-COIL), 4-1 (4-1-1 TO 4-1-7): SECOND TYPE SUB-COIL, 5-1 (5-1-1 TO 5-1-7): SECOND SUB-COIL (THIRD TYPE SUB-COIL), 5-4, 5-5: CROSS POINT, 5-6: FEEDING POINT, 6-1 (6-1-1 TO 6-1-6): FOURTH TYPE SUB-COIL, 7-1 (7-1-1 TO 7-1-6): FIFTH TYPE SUB-COIL, 19-3 (19-3-1 TO 19-3-8): SWITCHING CIRCUIT, 20-1: INNER SUPPORT, 20-2: OUTER SUPPORT, 50: MRI APPARATUS MAIN UNIT, 51: UPPER MAIN BODY, 52: LOWER MAIN BODY, 53: SUPPORT PART, 54: TABLE SURFACE, 55: BED PART, 61: TOP BOARD, 62: BED HOUSING, 101: MAGNET FOR GENERATING STATIC MAGNETIC FIELD, 102: GRADIENT MAGNETIC FIELD COIL, 103: SUBJECT (TEST OBJECT), 107: IRRADIATION COIL, 116 (116-1 TO 116-n): RECEIVER COIL, 104: SEQUENCER, 109: COMPUTER, 500: RECEIVER COIL UNIT, 550: OPENING, 551, 553: PLANAR FLAME, 552: CENTRAL CROSSPIECE, 510: PILLOW MEMBER, 600: BED COIL UNIT, 601: INSTALLATION SURFACE, 602: OPEN PART, 603: PREDETERMINED DISTANCE, 620: LOWER CASE, 621: UPPER CASE, 622: MAT PART, 623: RIM, 624: MOUNTING OPENING, 625: COIL ACCOMMODATION SPACE, 650: JOINT SUPPORT PART, 651: MAIN BODY OF JOINT SUPPORT, 652: FLANGE PART, 653: COIL MOUNTING SUPPORT PART, 700: UPPER COIL UNIT, 710: JOINING SECTION, 770: JOINT PART, 771: MAIN BODY OF JOINT PART, 772: COIL PROJECTION, 1001: FIRST PLANE

What is claimed is:

1. A magnetic resonance imaging apparatus comprising,
    a static magnetic field generation means for generating a static magnetic field in a vertical direction,
    an imaging means for applying an RF magnetic field and a gradient magnetic field to a test object placed in the static magnetic field, and
    a receiving means for receiving a nuclear magnetic resonance signal generated from the test object, the receiving means comprising a receiver coil unit made up of multiple types of sub-coils, wherein,
    the receiver coil unit comprises a bed coil unit whose longitudinal direction agrees with a body axis direction of the test object, and an upper coil unit which is detachably mounted on the bed coil unit,
    the bed coil unit comprises a carrying surface for placing the test object thereon, and multiple lower sub-coils arranged in a lower part of the carrying surface,
    the upper coil unit comprises multiple upper sub-coils which are connected to the lower sub-coils, and
    the upper sub-coils and the lower sub-coils are connected by mounting the upper coil unit on the bed coil unit to form the multiple types of sub-coils.

2. The magnetic resonance imaging apparatus according to claim 1, wherein,
    the upper sub-coils are separated into one arranged in a flexible inner support covering the carrying surface and another arranged in a flexible outer support covering an external side of the inner support.

3. The magnetic resonance imaging apparatus according to claim 2, wherein,
    the bed coil unit comprises multiple joint support parts formed on both sides of the carrying surface along the longitudinal direction, wherein,
    the upper coil unit includes a pair of joining sections having multiple joint parts connectable with the multiple joint support parts, the outer support whose both ends are supported by the pair of the joining sections, and a pair of inner supports each having one end mounted on the joining section, the other end being free end, and
    the joint support parts and the joint parts are connected to form the multiple sub-coils.

4. The magnetic resonance imaging apparatus according to claim 2, wherein,
the lower sub-coils arranged in the bed coil unit are divided into multiple blocks each having the same arrangement along the longitudinal direction, and
the upper coil unit is connected to one of the multiple blocks and forms independent multiple sub-coils for covering the external side of the test object placed on the installation surface.

5. The magnetic resonance imaging apparatus according to claim 4, wherein,
the inner support comprises an extending part which extends one end in the longitudinal direction, farther than the outer support, and
when multiple upper coil units are mounted on the bed coil unit along the longitudinal direction, the extending part overlaps the other end side of the inner support of other upper coil unit.

6. The magnetic resonance imaging apparatus according to claim 2, wherein,
the outer support comprises a sub-coil which has a coil conductor pattern existing above the test object, and the inner support comprises a sub-coil which has no coil conductor pattern existing above the test object.

7. The magnetic resonance imaging apparatus according to claim 2, wherein,
the multiple joint support parts formed along the longitudinal direction are provided in multiple rows on the both sides of the carrying surface.

8. A magnetic resonance imaging apparatus comprising a static magnetic field generation means for generating a static magnetic field in a vertical direction, an imaging means for applying an RF magnetic field and a gradient magnetic field to a test object placed in the static magnetic field, and a receiving means for receiving a nuclear magnetic resonance signal generated from the test object, the receiving means comprising a receiver coil unit made up of multiple types of sub-coils, wherein,
the receiver coil unit comprises a bed coil unit whose longitudinal direction agrees with a body axis direction of the test object, and multiple upper coil units detachably mounted on the bed coil unit along the longitudinal direction of the bed coil unit,
the bed coil unit comprises a carrying surface for placing the test object in the center of lateral direction which is orthogonal to the longitudinal direction, multiple joint support parts arranged along the longitudinal direction on the both sides of the lateral direction of the carrying surface, and multiple subsets of sub-coils connected with the joint support parts on both sides and arranged in the lateral direction,
the upper coil unit includes a pair of joining sections arranged on both sides of the lateral direction, an outer support whose ends are supported by the pair of the joining sections, and a pair of inner supports each having one end mounted on the joining section and the other end being free end,
the joining section has a stick-like appearance, and is provided with, along the longitudinal direction, multiple joint parts to be connected with the joint support parts,
the inner support and the outer support have a flexible thin plate-like appearance, a subset of sub-coils being arranged therein, and in each of the outer support and the inner support, multiple openings are formed in accordance with the arrangement of the sub-coils, and
the upper coil unit is allowed to be coupled with the bed coil unit via a linkage of the joint support parts and the joint parts, and the linkage forms multiple sub-coils which cover an external side of the test object placed on the carrying surface.

9. The magnetic resonance imaging apparatus according to claim 8, wherein,
the subsets of sub-coils arranged on the bed coil unit are divided into multiple blocks, each having an arrangement of the same subset of sub-coils along the longitudinal direction,
the upper coil unit is connected with one of the multiple blocks, and independent multiple sub-coils are formed to cover the external side of the test object placed on the carrying surface.

10. The magnetic resonance imaging apparatus according to claim 8, wherein,
the outer support comprises a sub-coil which has a coil conductor pattern existing above the test object, and the inner support comprises a sub-coil which has no coil conductor pattern existing above the test object.

11. The magnetic resonance imaging apparatus according to claim 8, wherein,
the inner support comprises an extending part which extends one end in the longitudinal direction, farther than the outer support, and
when the multiple upper coil units are mounted on the bed coil unit along the longitudinal direction, the extending part overlaps the other end side of the inner support of other upper coil unit.

12. The magnetic resonance imaging apparatus according to claim 8, wherein,
the multiple joint support parts are mounted rotatably so as to be opened in the lateral direction.

13. The magnetic resonance imaging apparatus according to claim 8, wherein,
the multiple joint support parts are provided in multiple rows on each of both sides of the lateral direction of the installation surface, and the multiple subsets of sub-coils are connected with the joint support parts in each of the multiple rows.

* * * * *